US009994508B2

(12) United States Patent
Lopez Perez et al.

(10) Patent No.: US 9,994,508 B2
(45) Date of Patent: Jun. 12, 2018

(54) VERSATILE AND FUNCTIONALISED INTERMEDIATES FOR THE SYNTHESIS OF VITAMIN D AND NOVEL VITAMIN D DERIVATIVES

(71) Applicant: Endotherm GmbH, Saarbruecken (DE)

(72) Inventors: Borja Lopez Perez, Santiago de Compostela (ES); Rita Sigueiro Ponte, Santiago de Compostela (ES); Miguel A. Maestro Saavedra, Santiago de Compostela (ES); Antonio Mourino Mosquera, Santiago de Compostela (ES)

(73) Assignee: Endotherm GmbH, Saarbruecken (DE)

( * ) Notice: Subject to any disclaimer, the term of this patent is extended or adjusted under 35 U.S.C. 154(b) by 0 days. days.

(21) Appl. No.: 14/650,904

(22) PCT Filed: Dec. 9, 2013

(86) PCT No.: PCT/ES2013/070859
§ 371 (c)(1),
(2) Date: Jul. 30, 2015

(87) PCT Pub. No.: WO2014/091046
PCT Pub. Date: Jun. 19, 2014

(65) Prior Publication Data
US 2015/0344421 A1    Dec. 3, 2015

(30) Foreign Application Priority Data

Dec. 11, 2012  (ES) .................................. 201231923

(51) Int. Cl.
*C07C 49/633* (2006.01)
*C07C 67/313* (2006.01)
*C07C 49/443* (2006.01)
*C07F 7/18* (2006.01)
*A61K 51/04* (2006.01)
*C07B 59/00* (2006.01)
*C07C 401/00* (2006.01)

(52) U.S. Cl.
CPC ........ *C07C 49/633* (2013.01); *A61K 51/0493* (2013.01); *C07B 59/001* (2013.01); *C07C 49/443* (2013.01); *C07C 67/313* (2013.01); *C07C 401/00* (2013.01); *C07F 7/1804* (2013.01); *C07F 7/1852* (2013.01); *C07F 7/1872* (2013.01); *C07C 2601/14* (2017.05); *C07C 2602/24* (2017.05)

(58) Field of Classification Search
CPC . C07C 401/00; C07C 2102/24; C07C 49/633; A61K 51/0493
See application file for complete search history.

(56) References Cited

U.S. PATENT DOCUMENTS

| 5,449,668 A | 9/1995 | Sestelo et al. |
| 6,075,015 A | 6/2000 | Sestelo et al. |
| 6,080,878 A | 6/2000 | de los Angeles Rey et al. |
| RE36,854 E | 9/2000 | Sestelo et al. |
| 2011/0213168 A1 | 9/2011 | Maestro Saavedra et al. |

FOREIGN PATENT DOCUMENTS

| EP | 0633245 A1 | 1/1995 |
| EP | 0884308 A2 | 4/1998 |
| EP | 2360154 A1 | 8/2011 |
| ES | 2094023 T3 | 1/1997 |
| ES | 2196476 T3 | 12/2003 |
| WO | 2006074227 A2 | 7/2006 |

OTHER PUBLICATIONS

Zaragoza Dorwald, Side Reactions in Organic Synthesis, Wiley-VCH Verlag GmbH & Co. KGaA, Weinheim, Preface. p. IX.*
Mao et al, Chemistry a European Journal, Diversity-Oriented Enantioselective Synthesis of Highly Functionalized, Cyclic and Bicyclic Alcohols, 2013, 19, pp. 761-S44.*
Smitrovich et al, Journal of the American Chemical Society, Copper-Mediated Substitution Reactions of Alkylmagnesium Reagents with Allylic Carbamates: (Z)-Selective Alkene Synthesis, 1998, 120, pp. 12998-12999.*
Sicinski et al., "Synthesis and Biological Activity of 1α,25-Dihydroxy-18-norvitamin D3 and 1α,25-Dihydroxy-18,19-dinorvitamin D3", J. Med. Chem. 1996, 39, 4497-4506.
Yamada et al., "Conformation-Function Relationship of Vitamin D: Conformational Analysis Predicts Potential Side-Chain Structure", J. Med. Chem. 1998, 41, 1467-1475.
Sas et al., "Total Synthesis of 1α,25-Dihydroxy-25-18-Norvitamin D3", Oct. 1997, SYNLETT, vol. 10, 1167-1170.
Gogoi et al., An Expeditious Route to 1α, 25-Dihydroxyvitamin D3 and Its Analogues by an Aqueous Tandem Palladium-Catalyzed A-Ring Closure and Suzuki Coupling to the C/D Unit, Chemistry: A European Journal, 2010, 16(5), 1432-1435.
Gogoi et al., Supporting Information: An Expeditious Route to 1α, 25-Dihydroxyvitamin D3 and Its Analogues by an Aqueous Tandem Palladium-Catalyzed A-Ring Closure and Suzuki Coupling to the C/D Unit, Chemistry: A European Journal, 2010, Journal, 2010, 16(5), 1432-1435.
Gregorio et al., Synthesis of two carboxylic haptens for raising antibodies to 25-hydroxyvitamin D3 and 1α, 25-dihydroxyvitamin D3, Journal of Steroid Biochemistry & Molecular Biology, 103, (2007), 227-230.
Hatcher et al., [3,3]—Sigmatropic rearrangments: short, stereocontrolled syntheses of functionalized vitamin D3 side-chain units, Tetrahedron Letters, 43 (2002), 5009-5012.
Gomez-Reino et al., Pd-Catalyzed Carbocyclization-Negishi Cross-Coupling Cascade: A Novel Approach to 1α, 25- Dihydroxyvitamin D3 and Analogues, Organic Letters, 2005, vol. 7, No. 26, 5885-5887.

(Continued)

*Primary Examiner* — Paul A Zucker
(74) *Attorney, Agent, or Firm* — Cahn & Samuels, LLP

(57) ABSTRACT

Novel intermediates for the complete synthesis of vitamin D are provided that allow a great versatility of functional groups in the final vitamin derivatives. Vitamin derivatives that are epimeric in position 3 and vitamin derivatives with a wide range of functionalities in position 18, including compounds with isotopic labelling are provided.

3 Claims, No Drawings

(56) References Cited

OTHER PUBLICATIONS

Holick, The Vitamin D Epidemic and its Health Consequences, Journal of Nutrition, 2005, 135(11), 2739S-2748S.
Chapleo et al., Synthetic Applications of Cyclic Orthoesters: Stereospecific Synthesis of a Bicyclic Alcohol related to the Vitamins D, J. Chem. Soc., Perkin 1, 1977, 1211-1218.
Trost et al., A Stereocontrolled Approach toward Vitamin D Metabolites, A Synthesis of the Inhoffen-Lythgoe Diol, J. Amer. Chem. Soc., 101:15, 1979, 4378-4380.
Johnson, et al., Asymmetric Sythnesis via Acetal Templates. A Stereoselective Approach to a Key Intermediate for the Preparation of Vitamin D Metabolites, J. Amer. Chem. Soc., 1984, 106, 1138-1139.
Stork, et al, A total synthesis of calcitriol, Pure & Appl. Chem., vol. 64, No. 12, 1992, 1809-1812.
Hatakeyama, et al., Enantioselective Synthesis of a C/D-Ring Synthon for the Preparation of Vitamin D3 Metabolites, J. Chem. Soc., Chem. Commun., 1989, 1893-1895.
Brandes, et al., Diastereoselection in an Aqueous Diels-Alder Reaction: a Formal Total Synthesis of the Inhoffen-Lythgoe Diol, J. Chem. Soc., Chem. Commun., 1988, 500-502.
Sikervar, et al., Intramolecular Methylation of an Allyl Sulfone via Lithium Alkoxyaluminate Application to the Enantioselective Synthesis of the CD Ring of Vitamin D3, Organic Letters, 2012, vol. 14, No. 11, 2922-2924.
Acs et al., The Synthesis of 13α-androsta-5,16-diene derivatives with carboxylic acid, ester and carboxamido functionalities at position-17 via palladium-catalyzed carbonylation, Steroids, 74, (2009), 419-423.
Goulioukina et al., A practical synthetic approach to chiral α-aryl substituted ethylphosphonates, Tetrahedron: Asymmetry, 12, (2001), 319-327.
Mascarenas, et al., A Short, Efficient Route to 1-Hydroxylated Vitamin D Ring A Fragments, Tetrahedron: Letters, vol. 33, No. 30, 1992, 4365-4368.
Lorock, Comprehensive Organic Transformations: A Guide to Functional Group Preparations, John Wiley & Sons, Inc., 2nd Edition, 1999, 689-700.
Lorock, Comprehensive Organic Transformations: A Guide to Functional Group Preparations, John Wiley & Sons, Inc., 2nd Edition, 1999, 1234-1248.
International Preliminary Report on Patentability, dated Jun. 2015.
International Written Opinion, dated Jan. 29, 2014.
English Abstract of EP 2360154.
English Abstract of EP 0633245.
English Abstract of EP 0884308.
English Abstract of ES 2094023.
English Abstract of ES 2196476.

* cited by examiner

VERSATILE AND FUNCTIONALISED INTERMEDIATES FOR THE SYNTHESIS OF VITAMIN D AND NOVEL VITAMIN D DERIVATIVES

FIELD OF THE INVENTION

This patent application is a U.S. national stage application of PCT international application PCT/ES2013/070859 filed on 9 Dec. 2013 and claims priority of Spanish patent document P201231923 filed on 11 Dec. 2012, the entirety of which is incorporated herein by reference.

The present invention is directed to compounds of formula I, to processes for the production thereof, to intermediates for their synthesis and methods of obtaining vitamin D derivatives and to novel derivatives of vitamin D.

BACKGROUND OF THE INVENTION

The preparation of vitamin D and its derivatives are historically addressed using different strategies. One, called classical pathway, is a linear synthesis employing as starting material a steroid (such as cholesterol) which after being hydroxylated at certain positions of the tetracycle and in the side chain (C-1 and C-25), it becomes a diene steroid $\Delta^{5-7}$(1α,25-dihydroxy-7-dehydrocholesterol) that, by irradiation with ultraviolet light, becomes the 1α, D3 25-dihidroxiprevitamina that evolves by heating to 1α,25-dihydroxyvitamin $D_3$. This photochemical-thermal process has low efficiency, due to the difficulties of preparing 7-dehydrointermediate performance and low photochemical process; and although some have already been optimized conditions, such as the wavelength of irradiation, filters and additives, it was only possible to obtain vitamin D in 47% yield. (M F, Brehm, J M, Alcorn, J F, Holguín, F, Aujla, S J, Celedón, J C (2005). "The Vitamin D Epidemic and its Health Consequences". *Journal of Nutrition* 135 (11): 2739S-2748S).

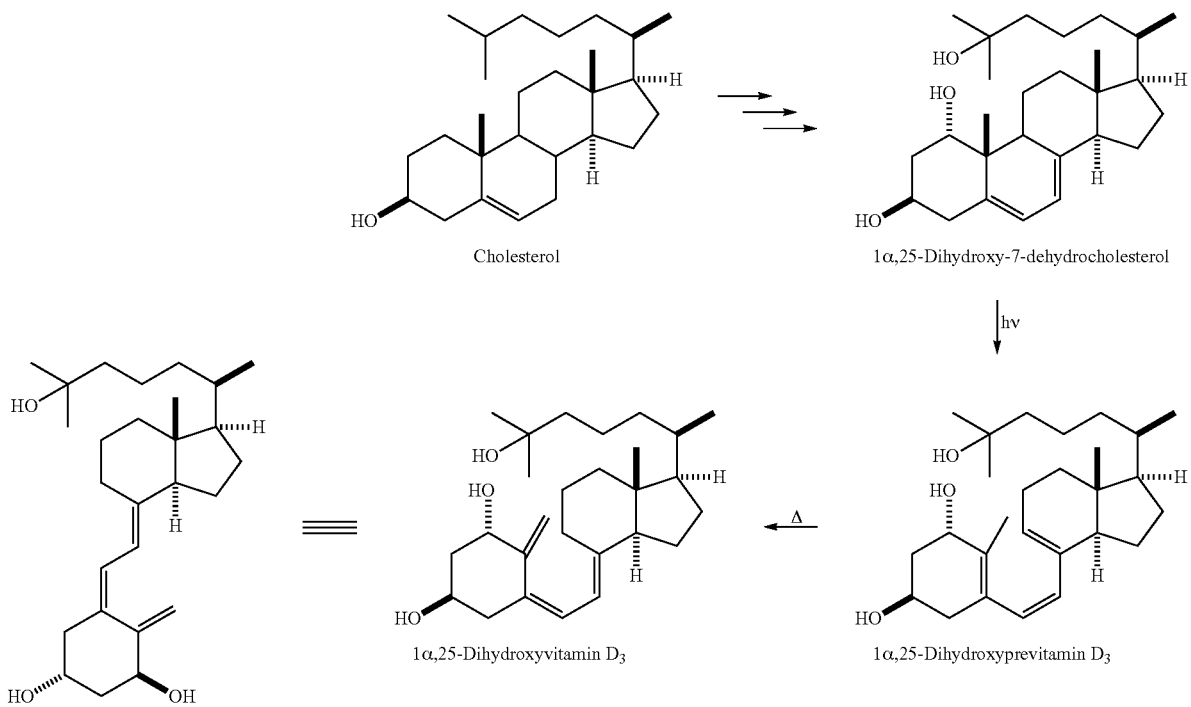

Further, this linear path requires complete synthesis start growing for each derivative of vitamin synthesis desired, and also these modifications in the structure leads to an increase in the number of steps and a decrease in overall performance.

Another common route is the convergent synthesis which uses as starting material a transhydrindane functionalized, known as Inhoffen-Lythgoe diol, which is the synthetic precursor bicycle CD with the side chain. The Inhoffen-Lythgoe diol is obtained by reductive ozonolysis of vitamin $D_2$. Vitamin $D_2$ turn is obtained from ergosterol, a steroid of plant origin. (Holick M F et al, (2005). "The Vitamin D Epidemic and its Health Consequences". *Journal of Nutrition* 135 (11): 2739S-2748S).

The preparation of vitamin D by total synthesis was also addressed. Overall, total synthesis strategies have addressed the synthesis of Inhoffen-Lythgoe diol, by synthetic routes using starting materials from various sources (acyl compounds, natural chiral compound "chiral pool", etc.), with highly stereoselective stages and a variable number of stages. Illustrative examples, listed below, correspond to the obtaining of Inhoffen-Lythgoe diol, except (d), in which the vitamin is prepared.

(a) Chapleo, C. B. et al, *J. Chem. Soc., Perkin Trans.* 1 1977, 1211-1218. Calciferol and Its Relatives. Part 19. Synthetic Applications of Cyclic Orthoesters: Stereospecific Synthesis of a Bicyclic Alcohol Related to the Vitamins D. Starting material: (S)-(−)-3-methylbutyrolactone, 13 steps, overall yield: 4%.

(b) Trost, B. M. el al, *J. Am. Chem. Soc.* 1979, 101, 4378-4380. A Stereocontrolled Approach Toward Vitamin D Metabolites. A Synthesis of the Inhoffen-Lythgoe Diol. Starting material: 3-carboxytricyclo[2.2.1.0$^{2,6}$]heptan-5-one, 11 steps, overall yield: 3%.
(c) Johnson, W. S. et al, *J. Am. Chem. Soc.* 1984, 106, 1138-1139. Asymmetric Synthesis via Acetal Templates. 6. A Stereoselective Approach to a Key Intermediate for the Preparation of Vitamin D Metabolites. Starting material: 8-bromo-6-methyl-oct-5-en-1-ine, 11 steps, overall yield: 14%.
(d) Stork, G. et al, *Pure Appl. Chem.* 1992, 64, 1809-1812. A Total Synthesis of Calcitriol. Starting material: 4-bromobutyraldehyde, 11 steps, overall yield: approx. 10%.
(e) Hatakeyama, S. et al, *J. Chem. Soc., Chem. Commun.* 1989, 1893-1895. Enantioselective Synthesis of a CD-Ring Synthon for the Preparation of Vitamin $D_3$ Metabolites. Starting material: cyclopropyl methyl ketone, 13 steps, overall yield: 4%.
(f) Brandes, E. et al, *J. Chem. Soc., Chem. Commun.* 1988, 500-502. Diastereoselection in an Aqueous Diels-Alder Reaction: a Formal Total Synthesis of the Inhoffen-Lythgoe Diol. Starting material: sodium (R)-(–)-methyl-3-hydroxypropionate, 20 steps, overall yield: 15%.
(g) Sikervar, V.; Fuchs, P. L. *Org. Lett.* 2012, 14, 2922-2924. Starting material: (S)-3-(phenylsulfonyl)-2,4-cyclohexadiene-1-ol, 12 steps, overall yield: 19%.

Although there are examples where vitamin D by fully chemical processes is prepared, these are still not very versatile and for each modification required in the substituents or in the stereochemistry of the same design should address and a new synthetic route to solve each particular approach.

BRIEF DESCRIPTION OF THE INVENTION

The authors of the present invention designed with high versatility intermediates allow preparation of vitamin D and its derivatives in few steps and with variations in both the nature of the substituents, including the isotopic labeling thereof, as in certain stereochemistry of certain carbons. The invention further provides a unique fully synthetic preparation process leading to vitamin D and many of its derivatives.

Thus, the present invention to compounds of formula (I) are highly functionalized very advanced intermediates in the synthesis of vitamin D and derivatives thereof is directed. More specifically, the functionality at C-25 can be prepared in a single step vitamin D and vitamin D derivatives with a wide variety of substituents. In particular, the compounds of formula (I) have substituents at the C-18 position, which are not present in other intermediate compounds or vitamin D derivatives of the prior technique. The substituent of the C-18 position can even be isotopically labelled. The intermediates of formula (I) of the invention are so versatile that they can be designed to suit the needs of your application and thus may also have R or S configuration at C-1 and C-3 positions. Functionality in C-25 also allows preparing radiolabelled derivatives at the end of the side chain, for example in the C-26 and C-27 positions, of a simple and fast way. The intermediates of formula (I) of the invention may further have R or S configuration at the C-20 position. The intermediates of formula (I) of the invention further may be unsaturated at C-16(17) position.

Thus, in one aspect the invention is directed to a compound of formula (I), their diastereoisomers or enantiomers

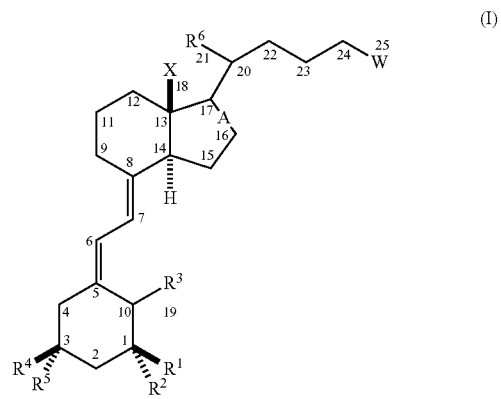

wherein each of $R^1$ and $R^2$ is independently selected from hydrogen, hydroxyl, alkoxy, aryloxy, alkylcarboxy, arylcarboxy and —OSiP$^1$P$^2$P$^3$,
$R^3$ is hydrogen or a methylene group (=CH$_2$),
each of $R^4$ and $R^5$ is independently selected from hydrogen, hydroxyl, alkoxy, aryloxy, alkylcarboxy, arylcarboxy and —OSiP$^1$P$^2$P$^3$, selected, at least one of $R^4$ and $R^5$ hydrogen,
X is selected from hydrogen, ($C_1$-$C_6$) alkyl, aryl, arylalkyl, heteroalkyl and heterocycle,
$R^6$ is selected from hydrogen and alkyl,
W is selected from —CO$_2$R$^a$, —CONR$^a$R$^b$ and —CN,
A represents a single or double bond,
each of $P^1$, $P^2$, $P^3$ is independently selected from alkyl, aryl, arylalkyl and heterocyclic,
each of R$^a$ and R$^b$ is independently selected from hydrogen, alkyl, alkenyl, alkynyl, aryl, arylalkyl and heterocyclic,
with the proviso that if A is a single bond then one of the following conditions is true: a) $R^5$ is hydrogen, or b) X is different from —CH$_3$, —CH$_2$CH$_3$, —CH$_2$OH, ethenyl and ethynyl.

It is also object of the present invention new derivatives of vitamin D with a variety of substituents and optionally may have the desired configuration at C-3 and C-20, which can be prepared from the intermediates described above.

Thus, in another aspect the invention is directed to a compound of formula (X), their diastereoisomers or enantiomers

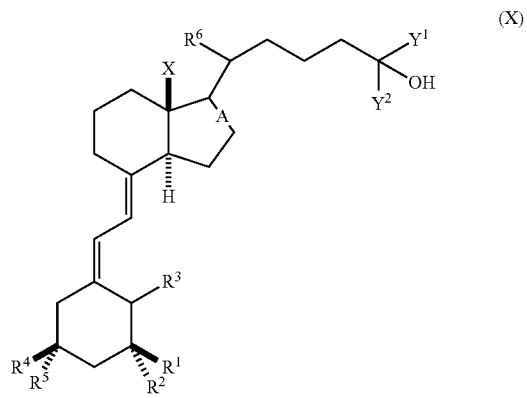

where $R^1$, $R^2$, $R^3$, $R^4$, $R^5$, $R^6$, X and A have the same values as defined above, and each of $Y^1$ and $Y^2$ is selected from hydrogen, ($C_1$-$C_6$) alkyl, aryl, arylalkyl, heterocycle, with the proviso that X is not —$CH_3$, —$CH_2CH_3$, —$CH_2OH$, ethenyl or ethynyl, and $Y^1$ and $Y^2$ are not isopropyl.

Other aspects of the invention are directed to intermediates useful in the preparation of compounds of formula (I) and (X).

Another aspect of the invention relates to the use of compounds of formula (I) and (X) as reference standards (internal standards) for spectrometric and spectroscopic techniques.

Another aspect of the invention relates to a pharmaceutical composition comprising the compounds of formula (X).

Another aspect of the invention relates to the use of a compound of formula (X) for the preparation of a medicament. Alternatively, the invention is directed to compounds of formula (X) for use as a medicament.

DETAILED DESCRIPTION OF THE INVENTION

Definitions

"Alkyl" refers to a straight or branched, cyclic or acyclic hydrocarbon chain formed by carbon atoms and hydrogen, without unsaturation, of 1 to 12, preferably eight, more preferably one to four carbon atoms, and which binds to remainder of the molecule by a single bond, which may optionally be isotopically labeled so that one or more hydrogens are replaced with deuterium ($^2H$) or tritium ($^3H$) and/or one or more carbons are replaced by carbon-11 ($^{11}C$), carbon-13 ($^{13}C$) or carbon-14 ($^{14}C$), optionally substituted by one or more substituents selected from the group consisting of a halogen atom, a hydroxy group, a carboxy group, an alkoxy group, a cyano group, nitro group, a thioalkoxy group, a heteroalkyl group, a heterocyclic group or $CF_3$, for example, methyl, ethyl, n-propyl, i-propyl, n-butyl, t-butyl, n-pentyl, cyclopropyl, etc.

"Alkenyl" refers to a straight or branched, cyclic or acyclic hydrocarbon chain consisting of carbon and hydrogen atoms, containing at least one unsaturation, conjugated or not, from 2 to 12, preferably from two to eight, more preferably two to four carbon atoms, and joins the rest of the molecule by a single bond and optionally can be isotopically labeled so that one or more hydrogens are replaced by $^2H$ or $^3H$ and/or one or more carbons are replaced by $^{11}C$, $^{13}C$ or $^{14}C$. Alkenyl radicals may be optionally substituted by one or more substituents such as a halogen atom, a halogen atom, a hydroxy group, a carboxy group, an alkoxy group, a cyano group, a nitro group, a thioalkoxy group, heteroalkyl group, a heterocyclic group or $CF_3$, for example, vinyl, allyl, butenyl (e.g. 1-butenyl, 2-butenyl, 3-butenyl), or pentenyl (e.g. 1-pentenyl, 2-pentenyl, 3- pentenyl, 4-pentenyl).

"Alkynyl" refers to a straight or branched, cyclic or acyclic hydrocarbon chain consisting of carbon and hydrogen atoms, containing at least one carbon-carbon triple bond, conjugated or not, from two to twelve, preferably two to eight, more preferably two to four carbon atoms, and joins the rest of the molecule by a single bond, such as —CCH, —$CH_2CCH$, —$CCCH_3$, —$CH_2CCCH_3$, and optionally can be isotopically labeled so that one or more hydrogens are replaced by $^2H$ or $^3H$ and/or one or more carbons are replaced by $^{11}C$, $^{13}C$ or $^{14}C$. The alkynyl radicals may be optionally substituted by one or more substituents such as a halogen atom, a hydroxy group, a carboxy group, an alkoxy group, a cyano group, a nitro group, a thioalkoxy group, a heterocyclic group or $CF_3$.

"Aryl" refers to an aromatic hydrocarbon of 6 to 10 carbon atoms, such as phenyl or naphthyl, and optionally can be isotopically labelled so that one or more hydrogens are replaced by $^2H$ or $^3H$ and / or one or more carbons They are replaced by $^{11}C$, $^{13}C$ or $^{14}C$. The aryl radical may be optionally substituted by one or more substituents selected from the group consisting of a halogen atom, a hydroxy group, a carboxy group, an alkoxy group, a cyano group, a nitro group, a thioalkoxy group, an alkyl group or $CF_3$.

"Arylalkyl" refers to one or more aryl groups attached to the remainder of the molecule via an alkyl radical, for example benzyl, 3-(phenyl) propyl, etc.

"Heterocycle" refers to a stable 3- to 15 members comprising carbon atoms and from 1 to 5 heteroatoms selected from nitrogen, oxygen and sulfur, preferably a 4 to 8 ring members comprising one or more heteroatoms, and preferably a 5- to 6 membered with one or more heteroatoms. For purposes of this invention, the heterocyclic groups may be monocyclic, bicyclic or tricyclic system that may include fused rings; and the nitrogen or sulfur in the heterocyclic ring may be optionally oxidized; the nitrogen atom may be optionally quarternized; and heterocyclic radical may be partially or fully saturated. The heterocyclic radicals may be aromatic (eg, may have one or more aromatic rings) in which case considered as "heteroaryl" for purposes of the present invention. The heterocyclic ring may be substituted by one or more substituents selected from the group consisting of a halogen atom, a hydroxy group, a carboxy group, an alkoxy group, an alkyl group, a thioalkoxy group, a cyano group, a nitro group or $CF_3$. Examples of such heterocycles include, for example, furan, thiophene, pyrrole, imidazole, triazole, isothiazole, benzothiophene, benzofuran, indole, benzimidazole, tetrahydrofuran.

"Alkoxy" refers to a radical of formula —O-alkyl, for example, methoxy, ethoxy, propoxy, etc.

"Aryloxy" refers to a radical of formula —O-aryl, for example phenoxy, benzyloxy, etc.

"Alkylcarboxy" refers to an alkyl group which joins the rest of the molecule through a carboxy group (—$CO_2$—).

"Arylcarboxy" refers to an aryl group which joins the rest of the molecule through a carboxy group (—$CO_2$—).

"Alkylacyl" refers to an alkyl group which joins the rest of the molecule via a carbonyl group (—CO—).

"Arylacyl" refers to an aryl group which joins the rest of the molecule via a carbonyl group (—CO—).

"Heteroalkyl" refers to an alkyl group in which one or more carbons are replaced by heteroatoms, preferably 1 to 5, wherein the heteroatom can be selected from oxygen, sulfur, selenium, tellurium, nitrogen, phosphorus, arsenic.

The compounds of the present invention may include diastereomers and/or enantiomers and racemic mixtures thereof, in the presence of chiral centers, and isomers depending on the presence of multiple bonds (e.g. Z, E). Such isomers, diastereomers, enantiomers and mixtures thereof are within the scope of the present invention.

Compounds of Formula (I)

Compounds of formula (I) are highly functionalized and compounds allow obtaining vitamin D derivatives with substituents on certain carbon different configuration and functional groups which can not be obtained efficiently from other known intermediates, as would be required greater number of synthetic steps and less overall performance.

The present invention also provides intermediates of vitamin D in which the functional group at C-25 is specifically selected to be in a single step to obtain compounds derived from vitamin D, and alpha (α) orientation in position C-3. They can also present a wide variety of substituents on positions C-1 and C-18, and having one of the two possible configurations at the C-20 position.

Preferred for the present invention, the intermediates of formula (I) wherein the C-3 position is a substituent in alpha position and $R^5$ is hydrogen. In a particular embodiment, $R^5$ in a compound of formula (I) is hydrogen.

In a particular embodiment, the compound of formula (I) is a compound of formula (Ia), their diastereoisomers or enantiomers

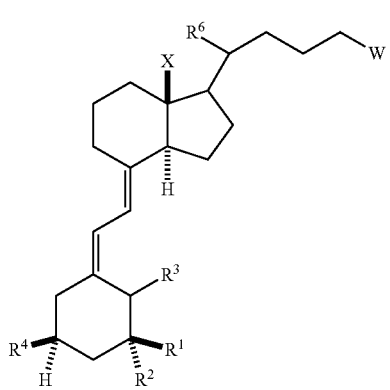

(Ia)

where $R^1$, $R^2$, $R^3$, $R^4$, $R^6$, X and W, have the same values as defined above.

The present invention also provides intermediates of vitamin D with a functional group at C-25 specifically selected so that in a single stage to obtain compounds derived from vitamin D and an unsaturation in the C-16(17) position. They can present a wide variety of substituents at positions as C-1, C-18 and having one of the two possible configurations at the C-20 position.

In a particular embodiment, the compound of formula (I) is a compound of formula (Ib), their diastereoisomers or enantiomers

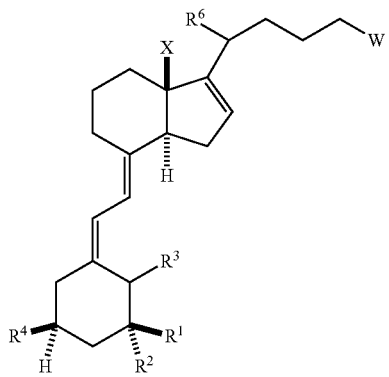

(Ib)

where $R^1$, $R^2$, $R^3$, $R^4$, $R^6$, X and W, have the same values as defined above.

In a particular embodiment, the compound of formula (I) is a compound of formula (Ic), their diastereoisomers or enantiomers

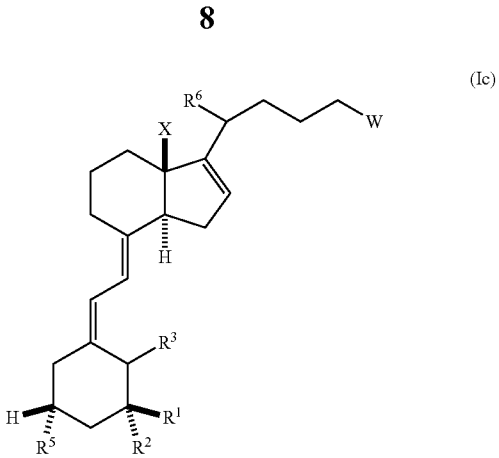

(Ic)

where $R^1$, $R^2$, $R^3$, $R^5$, $R^6$, X and W, have the same values as defined above.

The invention also provides intermediates of vitamin D with substituents of different nature in the C-18 position, and several possibilities at other positions of the structure, for example, have one of the two possible configurations at the C-20 position with a functional group at C-25 specifically selected to be in a single step they can obtain compounds derived from vitamin D.

In a particular embodiment, the compound of formula (I) is a compound of formula (Id), their diastereoisomers or enantiomers

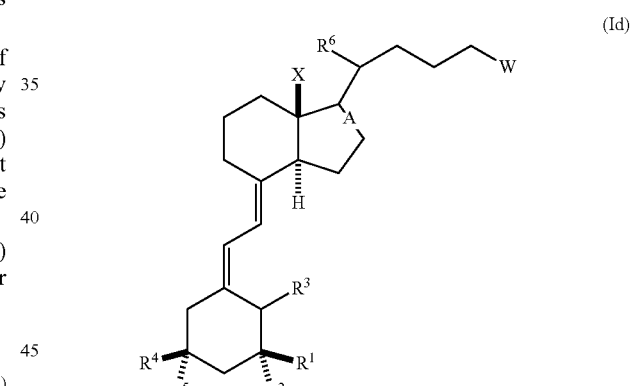

(Id)

where A, $R^1$, $R^2$, $R^3$, $R^4$, $R^5$, $R^6$, X and W, have the same values as defined above, with the proviso that X is not H, $CH_3$, $CH_2CH_3$, —$CH_2OH$, ethenyl and ethynyl.

In a particular embodiment, X in a compound of formula (I), (Ia), (Ib), (Ic) or (Id) is selected from ($C_3$-$C_6$) alkyl, aryl and arylalkyl. In a particular embodiment, X in a compound of formula (I), (Ia), (Ib), (Ic) or (Id) is selected from n-propyl, cyclopropyl, n-butyl, n-pentyl, n-hexyl, 2-(1,3-dioxolan-2-yl)-ethyl, phenyl and tolyl.

In a particular embodiment, $R^3$ in a compound of formula (I), (Ia), (Ib), (Ic) or (Id) is a methylene group.

In a particular embodiment, $R^4$ in a compound of formula (I), (Ia), (Ib) or (Id) is selected from hydroxyl, methoxy, benzyloxy, acetate, benzoate, propionate, butanoate, pivalate, triethylsilyloxy, tert-butyldimethylsilyloxy, benzyldimethylsilyloxy and tert-butyldiphenylsilyloxy; it is preferably hydroxyl.

In a particular embodiment, $R^5$ in a compound of formula (I) or (Id) is selected from hydroxyl, methoxy, benzyloxy, acetate, benzoate, propionate, butanoate, pivalate, triethylsilyloxy, tert-butyldimethylsilyloxy, benzyldimethylsilyloxy and tert-butyldiphenylsilyloxy; it is preferably hydroxyl.

In a particular embodiment, $R^1$ in a compound of (I), (Ia), (Ib), (Ic) or (Id) is selected from hydroxyl, methoxy, benzyloxy, acetate, benzoate, propionate, butanoate, pivalate, triethylsilyloxy, tert-butyldimethylsilyloxy, benzyldimethylsilyloxy and tert-butyldiphenylsilyloxy.

In a particular embodiment, $R^2$ in a compound of formula (I), (Ia), (Ib), (Ic) or (Id) is hydrogen.

In a more particular embodiment, $R^1$ in a compound of formula (I), (Ia), (Ib), (Ic) or (Id) is hydroxyl and $R^2$ is hydrogen.

In a more particular embodiment, $R^1$ and $R^2$ in a compound of formula (I), (Ia), (Ib), (Ic) or (Id) are hydrogen.

In a particular embodiment, W in a compound of formula (I), (Ia), (Ib), (Ic) or (Id) is —$CO_2R^a$, where $R^a$ is hydrogen or alkyl, preferably methyl, ethyl, n-propyl, i-propyl, n-butyl or t-butyl.

In a particular embodiment, W in a compound of formula (I), (Ia), (Ib), (Ic) or (Id) is —$CO_2R^a$, where $R^a$ is aryl, arylalkyl or heteroaryl, preferably phenyl or benzyl.

In a particular embodiment, $R^6$ in a compound of formula (I), (Ia), (Ib), (Ic) or (Id) is selected from hydrogen, $(C_1-C_4)$ alkyl, preferably methyl, ethyl, propyl, i-propyl, n-butyl or i-butyl. In a particular embodiment, $R^6$ has R or S configuration.

Isotopic Derivatives

Isotopic derivatives of the compounds of the invention are useful for use as internal standards in various mass spectrometry techniques or high-performance liquid chromatography coupled to nuclear magnetic resonance. The compounds of the invention incorporating $^{11}C$, $^{13}C$, $_{14}C$ or $^3H$ are also useful as radiopharmaceuticals, especially $^{11}C$ labelling is useful in the techniques of positron emission tomography (PET).

In the present invention, a compound "includes isotopic label" refers to a compound of the invention in which hydrogen atoms of between 1 and 9, are replaced by isotopes, deuterium or tritium and/or carbon atoms of between 1 and 9 are replaced by isotopes $^{11}C$, $^{13}C$, $^{14}C$.

The invention further provides compounds with permanent incorporation of isotope labeling C-18 in vitamin D and its derivatives. It is understood that permanent isotopic labeling that is not altered metabolism/catabolism of vitamin D and its derivatives in the human body; for example, it is known metabolic deactivation of 25-hydroxyvitamin $D_3$ and $1\alpha,25$-hydroxyvitamin $D_3$ by successive hydroxylations in the side chain to the calcitroic acid, which are lost C-23, C-24, C-25, C-26 and C-27 of the original vitamin, whereas if the isotopic label is located at C-18 would not occur loss of isotopic labelling by deactivation. Thus, it is of special interest for the invention compounds with permanent isotopic labeling.

Thus in another aspect the invention relates to compounds of formula (I), (Ia), (Ib), (Ic), (Id) or (X) wherein isotopic labelling incorporated for use as internal standards in spectroscopic and spectrometric techniques. Alternatively relates to the use of compounds of formula (I), (Ia), (Ib), (Ic), (Id) or (X) wherein isotopic labelling incorporated as internal standards in spectroscopic and spectrometric techniques.

In another aspect, the invention relates to compounds of formula (I), (Ia), (Ib), (Ic), (Id) or (X) wherein incorporate isotopic label selected from $^{11}C$, $^{13}C$, $_{14}C$ or $^3H$ for use as radiopharmaceuticals. Alternatively refers to the use of compounds of formula (I), (Ia), (Ib), (Ic), (Id) or (X) wherein incorporate labelling isotope selected from $^{11}C$, $^{13}C$, $_{14}C$ or $^3H$ as radiopharmaceuticals. Preferably, the compounds of formula (I), (Ia), (Ib), (Ic), (Id) or (X) wherein incorporate are useful as radiopharmaceuticals techniques positron emission tomography (PET).

In a particular embodiment, the isotopic labelling in the compounds of formula (I), (Ia), (Ib), (Ic), (Id) or (X) is incorporated in the X, $Y^1$ and/or $Y^2$ groups.

Thus, in another particular embodiment, X in a compound of formula (I), (Ia), (Ib), (Ic), (Id) or (X) is selected from the group consisting $(C_1-C_2)^2H_n$-alkyl, $(C_1-C_2)$ $^3H_n$-alkyl, $^2H/_n$-phenyl and $(C_1-C_4)$ alkyl or phenyl wherein one or more carbons are $^{11}C$, $^{13}C$, $_{14}C$, where n has a value between 1 and 6. In a further embodiment particularly X is selected from methyl-$^2H_3$, $^3H_3$-methyl, $^{13}C$-methyl, $^{13}C$-methyl-$^2H_3$, $^{11}C$-methyl, $^{14}C$-methyl, phenyl-$^2H_6$ and $^{13}C_n$-phenyl, where n has a value between 1 and 6.

In a particular embodiment, $Y^1$ and $Y^2$ groups in a compound of formula (X) are independently selected from the group $(C_1-C_2)$ $_2H_n$-alkyl, $(C_1-C_2)$ $^3H_n$-alkyl, and $(C_1-C_4)$ alkyl wherein one or more carbons are $^{11}C$, $^{13}C$, $_{14}C$. In a particular embodiment, $Y^1$ and $Y^2$ groups are selected from $^2H_3$-methyl, $^3H_3$-methyl, $^{13}C$-methyl, $^{13}C$-methyl-$^2H_3$, $^{11}C$-methyl and $^{14}$-methyl.

In a particular embodiment the compound of formula (I) is selected from the group consisting of:
3-epi-25-tert-butylester-1α-hydroxyvitamin $D_3$
3-epi-16-en-25-tert-butylester-1α-hydroxyvitamin $D_3$
3,20-diepi-25-tert-butylester-1α-hydroxyvitamin $D_3$
3,20-diepi-16-en-25-tert-butylester-1α-hydroxyvitamin $D_3$
3-epi-25-tert-butylester-vitamin $D_3$
3-epi-16-en-25-tert-butylester-vitamin $D_3$
3,20-diepi-25-tert-butylester-vitamin $D_3$
3,20-diepi-16-en-25-tert-butylester-vitamin $D_3$
18-trideutero-3-epi-25-tert-butylester-1α-hydroxyvitamin $D_3$
18-trideutero-3-epi-16-en-25-tert-butylester-1α-hydroxyvitamin $D_3$
18-trideutero-3,20-diepi-25-tert-butylester-1α-hydroxyvitamin $D_3$
18-trideutero-3,20-diepi-16-en-25-tert-butylester-1α-hydroxyvitamin $D_3$
18-trideutero-25-tert-butylester-1α-hydroxyvitamin $D_3$
18-trideutero-16-en-25-tert-butylester-1α-hydroxyvitamin $D_3$
18-trideutero-20-epi-25-tert-butylester-1α-hydroxyvitamin $D_3$
18-trideutero-20-epi-16-en-25-tert-butylester-1α-hydroxyvitamin $D_3$
18-trideutero-3-epi-25-tert-butylester-vitamin $D_3$
18-trideutero-3-epi-16-en-25-tert-butylester-vitamin $D_3$
18-trideutero-3,20-diepi-25-tert-butylester-vitamin $D_3$
18-trideutero-3,20-diepi-16-en-25-tert-butylester-vitamin $D_3$
18-trideutero-25-tert-butylester-vitamin $D_3$
18-trideutero-16-en-25-tert-butylester-vitamin $D_3$
18-trideutero-20-epi-25-tert-butylester-vitamin $D_3$
18-trideutero-20-epi-16-en-25-tert-butylester-vitamin $D_3$.

In a particular embodiment the compound of formula (X) is selected from the group consisting of:
18-trideutero-3-epi-1α,25-dihydroxyvitamin $D_3$
18-trideutero-3-epi-26,27-dihomo-1α,25-dihydroxyvitamin $D_3$
18-trideutero-3,20-diepi-1α,25-dihydroxyvitamin $D_3$
18-trideutero-3,20-diepi-26,27-dihomo-1α,25-dihydroxyvitamin $D_3$
18-trideutero-3-epi-16-en-1α,25-dihydroxyvitamin $D_3$ 18-trideutero-3-epi-26,27-dihomo-16-en-1α,25-dihydroxyvitamin $D_3$
18-trideutero-3,20-diepi-16-en-1α,25-dihydroxyvitamin $D_3$
18-trideutero-3,20-diepi-26,27-dihomo-16-en-1α,25-dihydroxyvitamin $D_3$
18-trideutero-1α,25-dihydroxyvitamin $D_3$
18,26,27-nonadeutero-1α,25-dihydroxyvitamin $D_3$
18-trideutero-20-epi-1α,25-dihydroxyvitamin $D_3$
18-trideutero-16-en-1α,25-dihydroxyvitamin $D_3$
18-trideutero-25-hydroxyvitamin $D_3$
18-trideutero-26,27-dihomo-25-hydroxyvitamin $D_3$
18,26,27-nonadeutero-25-hydroxyvitamin $D_3$
18-trideutero-20-epi-25-hydroxyvitamin $D_3$
18-trideutero-20-epi-26,27-dihomo-25-hydroxyvitamin $D_3$
18-trideutero-16-en-25-hydroxyvitamin $D_3$
18-trideutero-20-epi-16-en-25-hydroxyvitamin $D_3$
18-trideuterovitamin $D_3$
18,26,27-nonadeuterovitamin $D_3$
18-trideutero-20-epi-vitamin $D_3$
18-trideutero-16-en-vitamin $D_3$
18,26,27-nonadeutero-16-en-vitamin $D_3$
18-trideutero-20-epi-16-en-vitamin $D_3$
18,26,27-nonadeutero-20-epi-16-en-vitamin $D_3$ Synthesis of Compounds of Formula (I)

Another aspect of the invention relates to a process for the preparation of compounds of formula (I), which comprises a Wittig-Horner reaction between compounds (II) and (III) in presence of a base (II)

(III)

where $R^1$, $R^2$, $R^3$, $R^4$, $R^5$, $R^6$, X, W and A have the same values as defined above.

In another aspect, the invention is directed to an alternative process for preparing compounds of formula (I) where $R^3$ is methylene, comprising a coupling of compounds (IV) and (V) in the presence of a catalyst (IV)

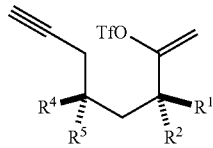

(V)

where $R^1$, $R^2$, $R^4$, $R^5$, $R^6$, X, W and A have the same values as defined above, and Z is selected from an indium halide a dialkyllindium, a diaryllithium, an alkylarylindium, a zinc halide, a dialkylboron or a dialkoxyboron.

The high functionalization of compounds of formula (I) that confer high versatility in preparing compounds derived from vitamin D, it is only possible to obtain from a compound of formula (II) and (IV) with the same high functionality. Accordingly, the intermediates of formula (VIII) are key since all and each of its functional groups is selected to allow high versatility of vitamin D derivatives of the present invention, and allows obtaining the compounds of formula (II) and (IV) efficiently and in a few stages.

In a particular embodiment, the invention relates to a process for preparing compounds of formula (II) described above from compounds of formula (VIIIa) or (VIIIb), comprising (VIIIa)

(VIIIb)

a) reduction of a W group of a compound of formula (VIIIa) or (VIIIb) to a $CH_2OH$ group,
b) halogenation of the hydroxyl group obtained in step a)
c) elongation of the side chain
d) deprotection
e) oxidation where $R^7$ is selected from alkyl, alkenyl, alkynyl, —$SiP^1P^2P^3$, arylalkyl, heterocyclic, alkylacyl and arylacyl, and $R^6$, X and W have the same values as defined above.

In a particular embodiment, the method further comprises an optional step between step a) and b) for reduction of the double bond In a particular embodiment, reduction to a $CH_2OH$ group is carried out using a reducing agent selected from a hydride, dissolved metal or metal salt, such as lithium aluminum hydride, sodium in ethanol with or without liquid ammonia, or samarium diiodide.

In a particular embodiment, the iodination is conducted in the presence of iodine and triphenylphosphine in basic medium or by the methods described in R. C. Larock. Comprehensive Organic Transformations. John Wiley & Sons, Inc. 2nd. edition, 1999, New York, pages 689-700.

In a particular embodiment, the side chain elongation is carried out in the presence of phosphoramide and an ester in a basic medium. In a more particular embodiment the phosphoramide is hexamethylphosphoramide. In another particular embodiment, the ester is selected from tert-butyl acetate, iso-butyl acetate, n-butyl acetate, iso-propyl acetate, n-propyl and ethyl acetate.

One skilled person in the technique can select different conditions for deprotection step d), where from group —$OR^7$ a hydroxyl is obtained. These conditions are selected depending on the value of $R^7$, for example between the conditions described in Wuts, P. G. M., Greene, T. W.; "Protective Groups in Organic Synthesis", 4rd Ed., John Wiley & Sons, Inc. 2007, New Jersey, pages 24-222. For example, in a case in which $R^7$ is trimethylsilyl, triethylsilyl, triisopropylsilyl, tert-butyldimethylsilyl, tert-butyldiphenylsilyl or tert-butyldimethylsilyl it is possible to carry out the deprotection by reaction with tetrabutylamonium fluoride, aqueous hydrofluoric acid solution or pyridinium fluoride.

A skilled person can select different conditions for carrying out the oxidation of step e) as described in R C Larock. Comprehensive Organic Transformations. John Wiley & Sons, Inc. 2nd. edition, 1999, New York, pages 1234-1248. For example it is possible to carry out the oxidation using the method of Swern or a derivative of chromium, for example pyridinium dichromate, pyridinium chlorochromate, chromium trioxide, chromic acid, or Dess-Martin periodinane or tetrapropylammonium perruthenate.

In a particular embodiment, reduction of the double bond takes place in the presence of a metal catalyst under hydrogen atmosphere or by hydrogen transfer. In a particular embodiment the metal catalyst is selected from palladium on carbon, platinum on carbon, rhodium on carbon, Raney nickel, and Wilkinson's catalyst.

The novel compounds of formula (VIIIa) and (VIIIb) are useful intermediates in the synthesis of compounds of formula (I) and compounds of formula (X). Thus in another aspect the invention relates to a compound of formula (VIIIa) or (VIIIb), their diastereoisomers or enantiomers.

In a particular embodiment, the invention relates to a process for the preparation of compounds of formula (VIIIa) comprising (1,4) reduction of a compound of formula (IX) in the presence of a chiral ligand,

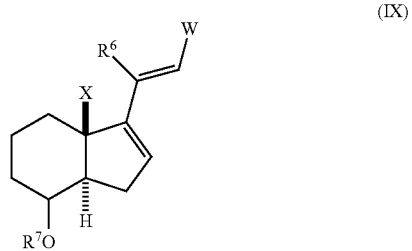

(IX)

where the chiral ligand is selected from (R)-1-[($R_P$)-2-(diphenylphosphino)ferrocenyl]ethyldi-tert-butylphosphine, (R)-(−)-5,5'-bis[di(3,5-di-tert-butyl-4-methoxyphenyl)phosphino]-4,4'-bi-1,3-benzodioxole or (R)-(−)-2,2'-bis[di(3,5-di-tert-butyl-4-methoxyphenyl)phosphino]-6,6'-dimethoxy-1,1'-biphenyl or (R)-(+)-2,2'-bis(diphenylphosphino)-1,1'-binaphtalene and where $R^7$, $R^6$, $P^1$, $P^2$, $P^3$, X and W have the same values as defined above.

In another particular embodiment, the invention relates to a process for the preparation of compounds of formula (VIIIb) comprising (1,4) reduction of a compound of formula (IX) in the presence of a chiral ligand, wherein the chiral ligand is selected from (S)-1-[($S_P$)-2-(diphenylphosphino)ferrocenyl]ethyldi-tert-butylphosphine, (S)-(−)-5,5'-bis[di(3,5-di-tert-butyl-4-methoxyphenyl)phosphino]-4,4'-bi-1,3-benzodioxole or (S)-(−)-2,2'-bis[di(3,5-di-tert-butyl-4-methoxyphenyl)phosphino]-6,6'-dimethoxy-1,1'-biphenyl or (S)-(−)-2,2'-bis(diphenylphosphino)-1,1'-binaphtalene.

Thus, from a compound of formula (IX) by (1,4) reduction of an ester α, β-unsaturated is possible to obtain a more advanced intermediate of formula (VIII). And, depending on the reducing conditions is possible to obtain a compound of formula (VIIIa) with a particular configuration at C-20 or the compound (VIIIb) with the opposite configuration at C-20. The conditions for performing the (1,4) reduction are known to a skilled person, for example using poly-(methylhydrosiloxane) in presence of a surfactant and a copper reagent. The side chain of a compound of formula (IX) leads to substituents with different configuration at the C-20 position and qualify unsaturation at C-16. The functional group at the chain stretching it allows a simple, fast and effective way. Compounds of formula (IX) are useful intermediates for access structures of vitamin D in fewer steps and with little complex reactions. Thus in another aspect the invention is directed to a compound of formula (IX) as defined above, their diastereomers or enantiomers.

In another aspect, the invention relates to a process for the preparation of intermediates of formula (IX) comprising a coupling reaction between a compound of formula (XI) and a compound of formula (XII) in the presence of a catalyst and optionally a base

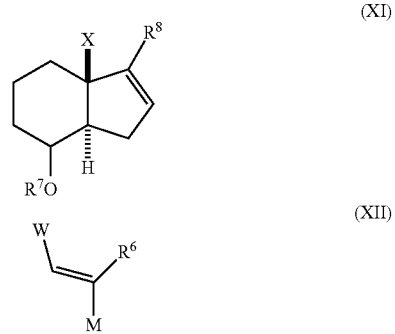

where X, W, $R^6$ and $R^7$ have the same values as defined above, $R^8$ is selected from alkyl sulfonate, arylsulfonate, halogen and phosphate, M is selected from hydrogen, Mg-Hal, Zn-Hal, B($OP^4$)$_2$, Sn($P^{4a}P^{4b}P^{4c}$), wherein Hal is chlorine, bromine or iodine, $P^4$ is selected from hydrogen, hydroxyl, alkyl, alkoxy, aryl, aralkyl and heterocycle, each of $P^{4a}$, $P^{4b}$, $P^{4c}$ is independently selected from alkyl, alkoxy, aryl, arylalkyl and heterocycle.

In a preferred embodiment, $R^8$ is selected from trifluoromethanesulfonate, methanesulfonate, benzenesulfonate, 4-methylbenzenesulfonate, 4-nitrobenzenesulfonate.

According to a preferred embodiment, the catalyst used is selected from the group of typical catalysts for the coupling reaction, for example and not limited to, Pd(OAc)$_2$, PdCl$_2$, Pd(PPh$_3$)$_4$, Pd(dba)$_2$, Ni(PPh$_3$)$_4$, Pd$_2$(dba)$_3$, Pd/C, (Ph$_3$P)

$_2$PdCl$_2$. The selection of this catalyst will depend on the other reaction conditions as described below in more detail.

According to another preferred embodiment, the coupling reaction is carried out in typical conditions known by skilled in the art. Preferably the coupling reaction is selected from the group of Heck reaction, Stille reaction, Suzuki reaction and Negishi reaction.

Preferably, when coupling reaction selected as the Heck reaction, in the compound of formula (XII), M is hydrogen; when selected Stille reaction, M is Sn(P$^{4a}$P$^{4b}$P$^{4c}$); when the Suzuki reaction is selected, M is B(OP$^4$)$_2$; Negishi reaction when selected, M is Zn-Hal. More preferably the coupling reaction is a Suzuki reaction and the compound of formula (XII) is a boron derivative, wherein M is B(OP$^4$)$_2$ In a preferred embodiment, the coupling reaction is conducted in the presence of a palladium catalyst selected from Pd(OAc)$_2$, PdCl$_2$, Pd(PPh$_3$)$_4$, Pd/C, Pd(dba)$_2$, Pd$_2$(dba)$_3$ and (Ph$_3$P)$_2$PdCl$_2$. In an even more preferred embodiment, also they added bases. These bases are selected from K$_3$PO$_4$, Ba(OH)$_2$, Cs$_2$CO$_3$, K$_2$CO$_3$, Bu$_4$F, TlOH, NaOH.

In a particular embodiment, the coupling reaction is a Suzuki reaction which is performed in the presence of (Ph$_3$P)$_2$PdCl$_2$ and potassium phosphate, wherein R$^8$ is trifluoromethanesulphonate and M is pinacolborane.

In a particular embodiment, the invention relates to a process for preparing compounds of formula (XI), comprising a) reacting a compound of formula (XIV) with an oxidizing agent in the presence of fluorine salt to obtain a compound of formula (XIII),

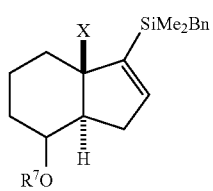

(XIV)

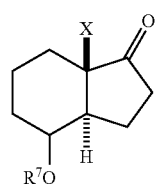

(XIII)

b) and, when R$^8$ is alkylsulfonate or arylsulfonate, reaction of a compound (XIII) and a carrier electrophilic agent alkylsulfonyl or arylsulfonyl group in the presence of a base, c) or when R$^8$ is halogen, a compound (XIII) is converted to the corresponding hydrazone and then reacted with a halogen in the presence of a guanidine, d) or when R$^8$ is phosphonate, the reaction of a compound (XIII) with phosphorus trichloride under acidic conditions and then reacted with an orthoformate, where X and R$^7$ have the same values as defined above.

In a particular embodiment, the oxidizing agent is selected from the most common oxidizing agents, for example, from the group consisting of hydrogen peroxide, m-chloroperbenzoic acid or peracetic acid.

In a particular embodiment, the fluorine salt is selected from the group consisting potassium fluoride, cesium fluoride, tetra-n-butylammonium trifluoride acetic acid complex hydrofluoride boron and boron trifluoride etherate.

In a particular embodiment, the carrier electrophile alkylsulfonyl group is a group trifluoromethanesulfonyl carrier electrophile.

In a particular embodiment, the carrier trifluoromethanesulfonyl group electrophile is selected from the group consisting of N-phenyl-bis(trifluoromethanesulfonimide), N-(5-chloro-2-pyridyl)bis(trifluoromethanesulfonimide), N-pyridyl-bis (trifluoromethanesulfonimide), trifluoromethanesulfonic anhydride, N-pyridyltriflimide and 5-chloro-N-pyridyltriflimide.

The transformation of ketone to hydrazones is known to one skilled in the art and conditions of this reaction and subsequent reaction with halogens can be found for example in P. Ács et al, *Steroids* 2009, 74, p. 420. The preparation of phosphonates from ketones is known to one skilled in the art and an example of the particular conditions can be found for example in N. S. Goulioukina et al, *Tetrahedron: Asymmetry* 2001, 12, p. 320.

In a particular embodiment, the invention relates to a process for preparing compounds of formula (XIV), comprising a) reacting a compound of formula (XV) with a base and an isocyanate, and

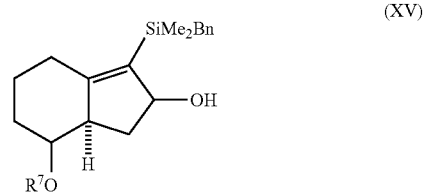

(XV)

b) adding a copper salt and X—Li to the mixture of step a), where X and R$^7$ have the same values as defined above.

In a particular embodiment, the base is selected from the group consisting of lithium diisopropylamide, methyllithium, ethyllithium, n-propyl lithium, i-propyl lithium, n-butyl lithium, hexyl lithium, phenyllithium, pyridine, triethylamine and ethyldiisopropylamine. Corresponding carbamate formation is achieved by adding a particular isocyanate which is selected from the group consisting of phenyl isocyanate, t-butyl isocyanate, p-methylphenylisocyanate and o-methylphenylisocyanate.

In a particular embodiment, the copper salt is selected from the group consisting of CuCl, CuBr, CuI, BrCu.SMe$_2$ and CuCN.

In a particular embodiment, X—Li is selected from the group consisting of (C$_1$-C$_6$) alkyl lithium, aryl lithium, arylalkyl lithium, heteroalkyl lithium and heterocycle lithium. In another particular embodiment, X—Li is selected from the group consisting of n-propyl lithium, cyclopropyl lithium, n-butyl lithium, n-pentyl lithium n-hexyl lithium, 2-(1,3-dioxolan-2-yl) -ethyl lithium, phenyl lithium and tolyl lithium.

In a particular embodiment, X—Li is selected from the group consisting of lithium $^2$H$_n$-alkyl (C$_1$-C$_2$) alkyl lithium $^3$H$_n$-(C$_1$-C$_2$), $^2$H$_n$-phenyl lithium and (C$_1$-C$_4$) alkyl lithium or phenyl lithium where one or more carbons are $^{11}$C, $^{13}$C or $^{14}$C, where n has a value from 1 to 6. In a particular embodiment X is selected from $^2$H$_3$-methyl lithium, $^3$H$_3$-methyl lithium, $^{13}$C-methyl lithium, $^{13}$C-methyl-$^2$H$_3$ lithium, $^{11}$C-methyl lithium, $^{14}$C-methyl lithium, $^{2}$H$_6$-phenyl lithium, $^{13}$C$_n$-phenyllithium, where n has a value between 1 and 6.

Some of the compounds X—Li are commercially available or are readily preparable from a general knowledge of the art that is familiar to one skilled in the art and comprises reacting the corresponding halogenated commercial compound by halogen-lithium exchange In a particular embodiment, the invention relates to a process for preparing compounds of formula (XV) which comprises reacting a compound of formula (XVI) with a reducing agent

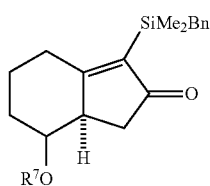

(XVI)

where R$^7$ has the same values as defined above.

In a particular embodiment, the reducing agent is a metal hydride, preferably selected from lithium aluminum hydride, diisobutylalumnium hydride, sodium (2-methoxyethoxy)aluminate, tri-s-butylborohydride, lithium borohydride, sodium borohydride and diborane.

In a particular embodiment, the invention relates to a process for preparing compounds of formula (XVI) comprising:
a) protect the hydroxyl of oct-1-en-7-yn-3-ol,
b) treating the resulting compound with a base and adding a silylating agent,
c) performing a Pauson-Khand reaction with the resultant compound of step b) using a CO donor metal complex and a co-oxidant.

The compound oct-1-en-7-yn-3-ol is known and their synthesis is described by Mascareñas, J. L.; Garcia, A. M.; Castedo, L.; Mourino, A. A short, efficient route to 1-hydroxylated vitamin D ring A. *Tet. Letters* 1992, 33, 4365.

One skilled in the art can select different conditions for protecting the hydroxyl group of oct-1-en-7-yn-3-ol in step a). These conditions are selected depending on the value of R$^7$, and the skilled person will employ reactions commonly employed in the field of organic chemistry, for example among the conditions described in Wuts, PGM, Greene, TW; "Protective Groups in Organic Synthesis", 4rd Ed., John Wiley & Sons, Inc. 2007, New Jersey, pages 24-222. For example, it is possible to carry out protection by reaction with t-butyldimethylsilyl chloride in the presence of a base such as imidazole.

In a particular embodiment, the silylating agent of step b) is selected from benzyldimethylsilyl chloride, t-butyldimethylsilyl chloride, t-butyldiphenylsilyl chloride, triisopropylsilyl chloride, trimethylsilyl chloride, t-butyldimethylsilyl triflate, triisopropylsilyl triflate, trimethylsilyl triflate.

In a particular embodiment, the CO donor metal complex is selected from the group consisting of Co$_2$(CO)$_8$, Fe(CO)$_5$, Ru$_2$(CO)$_{12}$, W(CO)$_6$, Mo(CO)$_6$, Cp$_2$TiR$_2$, Ni(COD)$_2$, [RhCl(CO)$_2$)]. In a particular embodiment, the co-oxidant is selected from N-methylmorpholine N-oxide, trimethylamine N-oxide, methylthioeters, hard Lewis bases. In a particular embodiment, in the Pauson-Khand reaction of step c) Co$_2$(CO)$_8$ is employed in presence of N-methylmorpholine N-oxide.

The compound of formula (X), as described above, can be obtained from compounds of formula (I) by a process comprising: a) reaction with Y$^1$—Li or Y$^1$—MgHal, b) reacting the resulting product of step a) with Y$^2$—Li or Y$^2$—MgHal, c) optionally deprotecting, where Hal is chlorine, bromine or iodine.

Some of the compounds Y$^1$—Li, Y$^1$—MgHal, Y$^2$—Li or Y$^2$—MgHal are commercially available or are readily preparable from a general knowledge of the art that is familiar to one skilled in the art and comprises reacting the corresponding halogenated commercial compound by halogen-metal exchange.

Step c) refers to the deprotection of the groups at positions 1 and 3 of the molecule, so that the groups R$^1$, R$^2$, R$^4$ and R$^5$ are hydroxyl after this step c). The deprotection conditions are known to one skilled in the art and general knowledge as reflected in Wuts, PGM, Greene, T W; "Protective Groups in Organic Synthesis", 4rd Ed., John Wiley & Sons, Inc. 2007, New Jersey, pages 24-222.

Another aspect of the invention relates to the use of a compound of formula (X) for the preparation of a medicament.

Compounds of formula (X) are suitable for the homeostasis of calcium and phosphorus, thus for treating diseases of the skeleton and musculature, for example, osteoporosis, osteopenia, fracture risk; for the regulation of cell proliferation and differentiation, treatment of cancer; for regulating the immune system and for the treatment of psoriasis. In a particular aspect the invention is directed to the use of compounds of formula (X) for the preparation of a medicament for the regulation of calcium and phosphorus, for the treatment of cancer or to treat immune system diseases.

Alternatively, in a particular aspect, the invention is directed to compounds of formula (X) for use in the regulation of calcium and phosphorus in mammals.

In another particular aspect, the invention is directed to compounds of formula (X) for use in treating cancer.

In a particular aspect, the invention is directed to compounds of formula (X) for use to treat immune system diseases. In a more particular aspect, for use in the treatment of psoriasis.

The following examples illustrate the invention and should not be understood as limiting thereof.

EXAMPLE 1

Oct-1-en-7-yn-3-ol (rac-1)

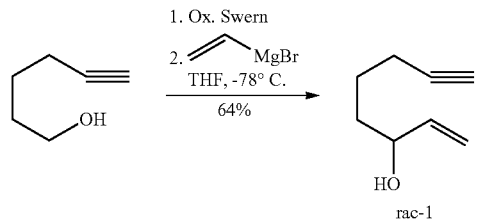

DMSO (3.62 mL, 50.9 mmol) was added to a solution of (COCl)$_2$ (1.89 mL, 22.4 mmol) in CH$_2$Cl$_2$ (20 mL). The mixture was cooled to −78° C. It was stirred for 15 min and a solution of 5-hexyn-1-ol (1.12 mL, 10.18 mmol) in CH$_2$Cl$_2$ (20 mL) was added. It was stirred and NEt$_3$ (14.11 mL, 101.8 mmol) was successively added. The mixture was allowed to reach room temperature and was then quenched by the addition of saturated aqueous NH₄Cl. The aqueous layer was extracted with CH₂Cl₂. The oil was dissolved in ethyl ether (Et₂O) (110 mL) was added to a solution of vinylmagnesium bromide in tetrahydrofuran (THF) (81 mL, 1M, 81 mmol) cooled to −78° C. After 16 h the reaction was quenched by the addition of a saturated solution NH₄Cl. The aqueous phase was extracted with Et₂O and the concentrate was purified by column chromatography (SiO₂, 12% EtOAc/hexanes) to afford rac-1 [0.809 g, 64%, colorless oil]. ¹H-NMR (CDCl₃, 250 MHz): δ=5.82 (1H, ddd, J=16.8, 10.4, 6.3, H-2), 5.18 (1H, dd, J=17.2, 1.5, H-1), 5.07 (1H, dd, J=10.4, 1.4, H-1), 4.07 (m, 1H, H-3), 1.93 (1H, m, H-8).

EXAMPLE 2

(3)-tert-Butyldimethyl(oct-1-en-7-yn-3-yloxy)silane (rac-2)

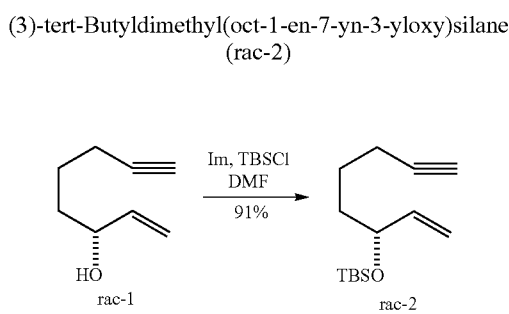

Imidazole (1.19 g, 17.52 mmol) and tert-butyldimethylsilyl chloride (TBSCl) (1.26 g, 8.38 mmol) were successively added to a solution of rac-1 (0.772 g, 6.22 mmol) in dimethylformamide (DMF) (30 mL). The reaction mixture was stirred at room temperature. A saturated NaCl solution was added. It was extracted with hexanes and the organic phase was concentrated and purified by flash chromatography (SiO₂, 10% Et₂O/hexanes) to afford rac-2 [1.364 g, 92%, oily liquid]. ¹H NMR (250 MHz, CDCl₃): δ=5.80 (1H, ddd, J=16.7, 10.4, 6.0, H-2), 5.15 (1H, d, J=17.2, H-1), 4.98 (1H, d, J=10.4, H-1), 4.10 (1H, m, H-3), 2.20 (1H, m,), 1.96 (1H, mH-8), 0.86 (9H, s, ᵗBuSi), 0.07 (3H, s, CH₃Si), 0.05 (3H, s, CH₃SI).

EXAMPLE 3

(7)-Benzyl (6-(tert-butyldimethysilyloxy)oct-7-en-1-yn-1-yl)dimethylsilane (rac-3)

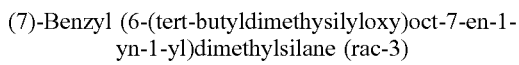

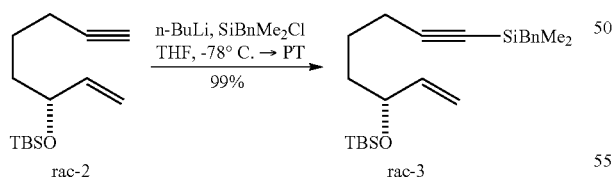

A solution of ⁿBuLi in hexanes (0.41 mL, 2.5 M, 1.02 mmol) was added dropwise to a solution of rac-2 (0.203 g, 0.85 mmol) in THF (6 mL) at −78° C. It was stirred and benzyldimethylsilylchloride (Me₂BnSiCl) (0.20 mL, 1.11 mmol) was added dropwise. The reaction was quenched with saturated aqueous NaCl. The aqueous layer was extracted with hexanes. The organic phase was concentrated and purified by column chromatography (SiO₂, hexanes) to afford rac-3 [0.327 g, 99%, colorless oil]. ¹H NMR (250 MHz, CDCl₃): δ=7.23 (2H, m, H_{ar}), 7.10 (1H, m, H_{ar}), 7.08 (2H, m, H_{ar}), 5.81 (1H, ddd, J=17.3, 10.3, 5.9, H-7), 5.18 (1H, d, J=17.1, H-8), 5.06 (1H, d, J=10.6, H-8), 4.14 (1H, m, H-6), 2.31 (2H, m), 2.19 (2H, s, CH₂Bn), 1.59 (4H, m), 0.93 (9H, s, ᵗBuSi), 0.12 (6H, s, 2×CH₃Siᵗbu), 0.09 (3H, s, CH₃SiBn), 0.07 (3H, s, CH₃SiBn).

EXAMPLE 4

(7,7a)-3-Benzyldimethylsilyl)-7-(tert-butyldimethylsilyloxy)-5,6,7,7a-tetrahydro-1H-inden-2(4H)-one (rac-4)

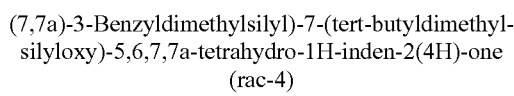

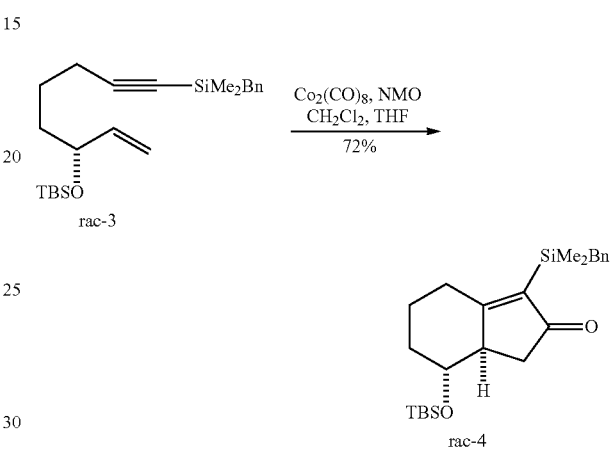

Co₂(CO)₈ (1.490 g, 4.36 mmol) was added to a solution of rac-3 (0.991 g, 2.56 mmol) in CH₂Cl₂ (12 mL). CH₂Cl₂ (23 mL) and THF (35 mL) were added and the mixture was cooled at 0° C. N-Methylmorpholine N-oxide (NMO) (3.603 g, 30.76 mmol) was added. A solution of 10% ethyl acetate/hexanes was added and the mixture was filtered, concentrated and was purified by column chromatography (SiO₂, hexanes) to afford rac-4 [0.848 g, 80%, colorless liquid]. ¹H NMR (250 MHz, CDCl₃): δ=7.16 (2H, t, J=7.3, H_{ar}), 7.05 (1H, t, J=7.3, H_{ar}), 6.94 (2H, d, J=6.6, H_{ar}), 3.10 (1H, td, J=10.6, 4, H-7), 2.60 (2H, m), 2.47 (1H, m), 2.34 (1H, m), 2.23 (1H, m), 1.85 (2H, m), 1.63 (2H, s, CH₂Ph), 0.88 (9H, s, ᵗBuSi), 0.22 (6H, s, 2×CH₃Siᵗbu), 0.06 (3H, s, CH₃SiBn), 0.04 (3H, s, CH₃SiBn).

EXAMPLE 5

(2,7,7a)-3-(Benzyldimethylsilyl)-7-(tert-butyldimethylsilyloxy)-2,4,5,6,7,7a-hexahydro-1H-inden-2-ol (rac-5)

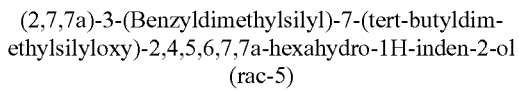

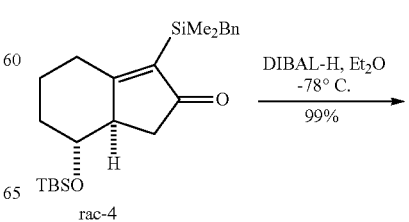

-continued

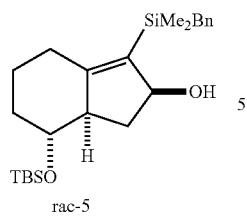
rac-5

A solution of DIBAL-H in CH$_2$Cl$_2$ (2.11 mL, 1 M, 2.11 mmol) was added to a solution of rac-4 (0.350 g, 0.84 mmol) in Et$_2$O (17 mL) at −78° C. After one hour HCl (5%) was added and the mixture was extracted with methyl-tert-butyl ether (MTBE). The organic phase was dried, filtered, concentrated and purified by column chromatography (SiO$_2$, 3% ethyl acetate/hexanes) to afford rac-5 [0.349 g, 99%]. $^1$H NMR (250 MHz, CDCl$_3$): δ=7.20 (2H, t, J=7.3, H$_{ar}$), 7.09 (1H, t, J=7.3, H$_{ar}$), 7.01 (2H, d, J=6.8, H$_{ar}$), 4.72 (1H, sa, H-2), 3.25 (1H, td, J=9.9, 4.0, H-7), 2.4 (2H, m), 2.24 (2H, s, CH$_2$Ph), 0.91 (9H, s, $^t$BuSi), 0.19 (3H, s), 0.17 (3H, s), 0.10 (3H, s), 0.09 (3H, s).

EXAMPLE 6

Benzyl [(3a,7,7a)-7-(tert-butyldimethylsilyl)oxy)-3a-methyl-3a,4,5,6,7,7a-hexahydro-1'-inden-3-yl]dimethylsilane (rac-6)

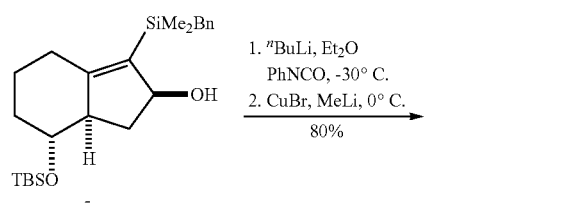

A solution of $^n$BuLi in hexanes (0.62 mL, 1.4 M, 0.869 mmol) was added to a solution of rac-5 (0.345 g, 0.828 mmol) in Et$_2$O (10 mL) at −30° C. Phenylisocyanate (PhNCO) (0.099 mL, 0.911 mmol) was added. The mixture was stirred at RT and CuBr (0.119 g, 0.828 mmol) was added. A solution of MeLi (0.569 mL, 0.911 mmol) was added at 0° C. After 12 h, a solution of MeLi in Et$_2$O (0.569 mL, 1.6 M, 0.911 mmol) was added at 0° C. After stirring for 36h, a saturated aqueous solution of NH$_4$Cl was added. The aqueous phase was extracted with methyl-tert-butyl ether, it was concentrated and purified by flash chromatography (SiO$_2$, hexanes) to afford rac-6 [0.274 g, 80%, colorless oil]. $^1$H NMR (250 MHz, CDCl$_3$): δ=7.20 (2H, t, J=7.3, H$_{ar}$), 7.07 (1H, t, J=7.3, H$_{ar}$), 7.01 (2H, d, J=6.8, H$_{ar}$), 6.02 (1H, bs, C-16), 3.78 (1H, td, J=10.5, 4.5, H-7), 2.33 (1H, m, H-7a), 2.18 (2H, s, CH$_2$Ph), 0.91 (9H, s, $^t$BuSi), 0.80 (3H, s, H-8), 0.08 (6H, s), 0.06 (3H, s), 0.03 (3H, s).

EXAMPLE 7

Benzyl [(3a,7,7a)-7-(tert-butyldimethylsilyl)oxy)-3a-trideuteromethyl-3a,4,5,6,7,7a-hexahydro-1H-inden-3-yl]dimethylsilane (rac-7)

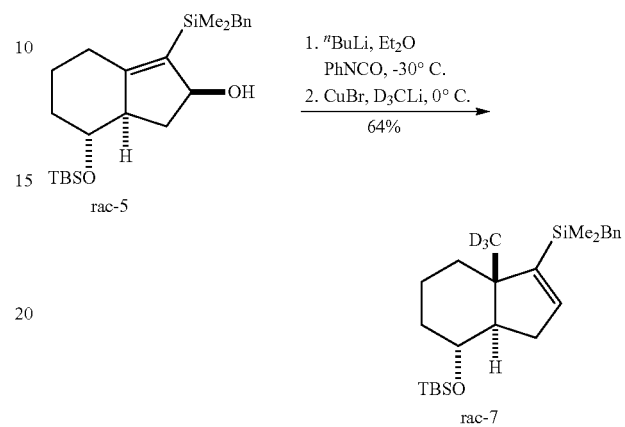

It is obtained by following the preparation of benzyl [(3a,7,7a)-7-(tert-butyldimethylsilyl)oxy)-3a-methyl-3a,4,5,6,7,7a-hexahydro-1H-inden-3-yl]dimethylsilane (rac-6) using rac-5 (0.094 g, 0.227 mmol), $^n$BuLi (0.18 mL, 1.3 M, 0.238 mmol), PhNCO (0.027 mL, 0.250 mmol), CuBr (0.036 g, 0.250 mmol) and CD$_3$Li in Et$_2$O (1.51 mL, 0.3 M, 0.454 mmol) to give rac-7 [0.061 g, 64%, yellow oil]. $^1$H NMR (400 MHz, CDCl$_3$): δ=7.20 (2H, t, J=7.3, H$_{ar}$), 7.07 (1H, t, J=7.3, H$_{ar}$), 7.01 (2H, d, J=6.8, H$_{ar}$), 6.02 (1H, bs, C-16), 3.78 (1H, td, J=10.5, 4.5, H-7), 2.33 (1H, m, H-7a), 2.18 (2H, s, CH$_2$Ph), 0.91 (9H, s, $^t$BuSi), 0.08 (6H, s), 0.06 (3H, s), 0.03 (3H, s).

EXAMPLE 8

Benzyl [(3a,7,7a)-7-(tert-butyldimethylsilyl)oxy)-3a-ethyl-3a,4,5,6,7,7a-hexahydro-1H-inden-3-yl]dimethylsilane (rac-8)

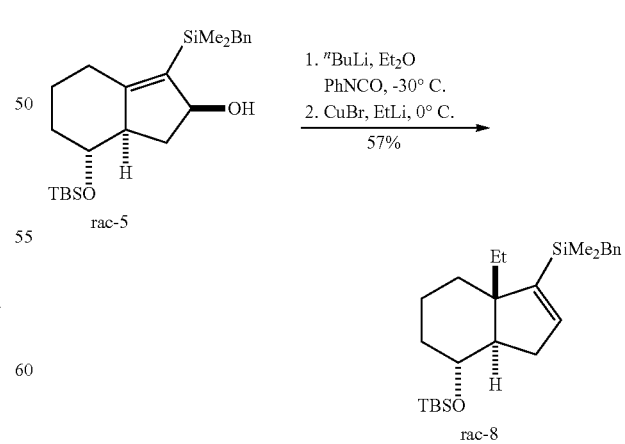

It is obtained by following the preparation of benzyl [(3a,7,7a)-7-(tert-butyldimethylsilyl)oxy)-3a-methyl-3a,4,5,6,7,7a-hexahydro-1H-inden-3-yl]dimethylsilane (rac-6)

using rac-5 (0.087 g, 0.210 mmol), "BuLi (0.169 mL, 1.3 M, 0.220 mmol), PhNCO (0.025 mL, 0.231 mmol), CuBr (0.030 g, 0.210 mmol), and EtLi in benzene/cyclohexane (0.954 mL, 0.5 M, 0.462 mmol) to give rac-8 [0.051 g, 57%, yellowish oil]. ¹H-NMR (400 MHz, CDCl₃): δ=7.20 (2H, t, J=7.3, H$_{ar}$), 7.06 (1H, t, J=7.3, H$_{ar}$), 7.00 (2H, d, J=6.6, H$_{ar}$), 5.98 (1H, t, C-16), 3.59 (1H, dt, J=7.4, 2.8, H-7), 2.43 (1H, m, H-7a), 2.19 (2H, s, CH₂Ph), 2.13 (1H, m), 1.96 (1H, q m), 1.70 (3H, m), 1.42 (2h, m), 0.89 (9H, s, $^t$BuSi), 0.82 (3H, t, J=7.3, CH₂$\underline{CH_3}$), 0.04 (6H, s), 0.03 (3H, s), 0.03 (3H, s).

EXAMPLE 9

Benzyl [(3a,7,7a)-7-(tert-butyldimethylsilyl)oxy)-3a-butyl-3a,4,5,6,7,7a-hexahydro-1H-inden-3-yl]dimethylsilane (rac-9)

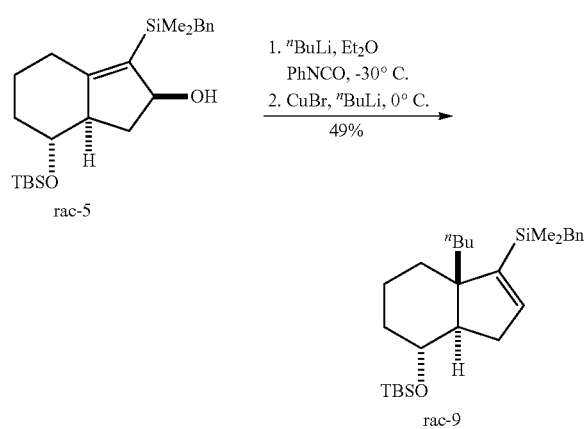

It is obtained by following the preparation of benzyl [(3a,7,7a)-7-(tert-butyldimethylsilyl)oxy)-3-a-methyl-3a,4,5,6,7,7a-hexahydro-1H-inden-3-yl]dimethylsilane (rac-6) using rac-5 (0.097 g, 0.234 mmol), "BuLi (0.189 mL, 1.3 M, 0.246 mmol), PhNCO (0.030 mL, 0.257 mmol), CuBr (0.034 g, 0.234 mmol) and $^t$BuLi (0.396 mL, 1.3 M, 0.541 mmol) to yield rac-9 [0.052 g, 49%, yellow oil]. ¹H NMR (400 MHz, CDCl₃): δ=7.20 (2H, t, J=7.3, H$_{ar}$), 7.08 (1H, t, J=7.3, H$_{ar}$), 6.99 (2H, d, J=6.6, H$_{ar}$), 6.13 (1H, bs, C-2), 3.84 (1H, td, J=10.4, 4.6, H-7), 2.15 (2H, s, CH₂Ph), 0.89 (9H, s, $^t$BuSi), 0.07 (6H, s), 0.04 (6H, s).

EXAMPLE 10

Benzyl [(3a,7,7a)-3a-hexyl-7-((tert-butyldimethylsilyl)oxy)-3a,4,5,6,7,7a-hexahydro-1H-inden-3-yl]dimethylsilane (rac-10)

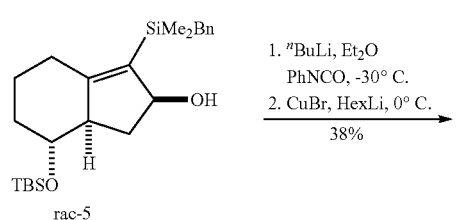

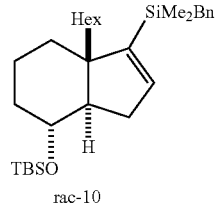

It is obtained by following the preparation of benzyl [(3a,7,7a)-7-(tert-butyldimethylsilyl)oxy)-3 a-methyl-3a,4,5,6,7,7a-hexahydro-1H-inden-3-yl]dimethylsilane (rac-6) using rac-5 (0.096 g, 0.230 mmol), "BuLi (0.172 mL, 1.41 M, 0.242 mmol), PhNCO (0.027 mL, 0.253 mmol), CuBr (0.033 g, 0.230 mmol) and "HexLi in hexanes (0.110 mL, 2.3 M, 0.253 mmol) to give rac-10 [0.042 g, 38%, yellow oil]. ¹H NMR (400 MHz, CDCl₃): δ=7.19 (2H, t, J=7.3, H$_{ar}$), 7.06 (1H, t, J=7.3, H$_{ar}$), 6.98 (2H, d, J=7.3, H$_{ar}$), 6.13 (1H, bs, H-2), 3.84 (1H, td, J=10.4, 4.5, H-7), 2.15 (2H, s, CH₂Ph), 0.89 (9H, s, $^t$BuSi), 0.06 (6H, s), 0.04 (6H, s).

EXAMPLE 11

Benzyl (3a,7,7a)-7-[(tert-butyldimethylsilyl)oxy)-3a-cyclopropyl-3a,4,5,6,7,7a-hexahydro-1H-inden-3-yl]dimethylsilane (rac-11)

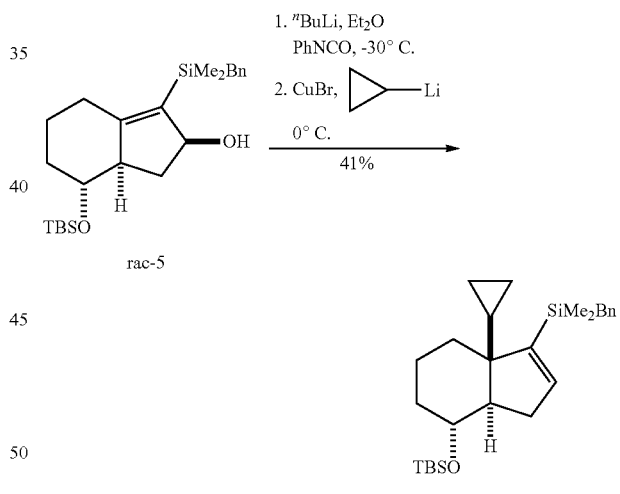

It is obtained by following the preparation of benzyl [(3a,7,7a)-7-(tert-butyldimethylsilyl)oxy)-3a-methyl-3a,4,5,6,7,7a-hexahydro-1H-inden-3-yl]dimethylsilane (rac-6) using rac-5 (0.110 g, 0.264 mmol), "BuLi (0.197 mL, 1.41 M, 0.277 mmol), PhNCO (0.032 mL, 0.290 mmol), CuBr (0.040 g, 0.277 mmol) and cyclopropyl lithium in Et₂O (1.12 mL, 0.26 M, 0.290 mmol) to give rac-11 [0.048 g, 41%, yellow oil]. ¹H NMR (400 MHz, CDCl₃): δ=7.19 (2H, t, J=7.3, H$_{ar}$), 7.06 (1H, t, J=7.3, H$_{ar}$), 6.96 (2H, d, J=7.3, H$_{ar}$), 6.20 (1H, m, C-2), 4.07 (1H, td, J=10.4, 4.4, H-7), 2.11 (2H, s, CH₂Ph), 0.90 (9H, s, $^t$BuSi), 0.32 (1H, m, CyPr), 0.21 (1H, m, CyPr), 0.07 (6H, s), 0.05 (3H, s), 0.03 (3H, s), −0.17 (1H, m, CyPr).

EXAMPLE 12

[((3a,7,7a)-3a-(2'-(1',3'-Dioxolan-2'-yl)ethyl)-3-(benzyldimethylsilyl)-3a,4,5,6,7,7a-hexahydro-1H-inden-7-yl)oxy](tert-butyl)dimethylsilane (rac-12)

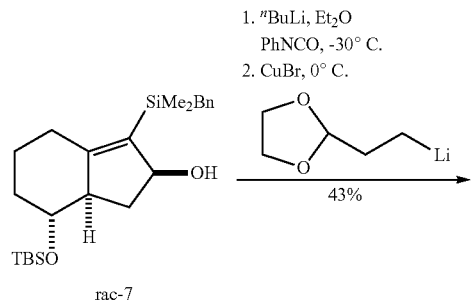

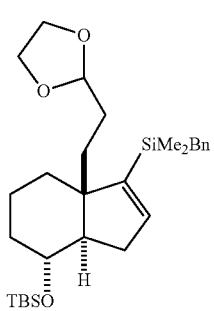

It is obtained by following the preparation of benzyl [(3a,7,7a)-7-(tert-butyldimethylsilyl)oxy)-3a-methyl-3a,4,5,6,7,7a-hexahydro-1H-inden-3-yl]dimethylsilane (rac-6) using rac-5 (0.095 g, 0.228 mmol), "BuLi (0.170 mL, 1.41 M, 0.239 mmol), PhNCO (0.027 mL, 0.251 mmol), CuBr (0.033 g, 0.228 mmol) and (2-(1,3-dioxolan-2-yl)ethyl) lithium in Et$_2$O (0.660 mL, 0.38 M, 0.251 mmol) to give rac-12 [0.049 g, 43%, yellow oil]. $^1$H NMR (400 MHz, CDCl$_3$): δ=7.19 (2H, t, J=7.3, H$_{ar}$), 7.06 (1H, t, J=7.3, H$_{ar}$), 6.98 (2H, d, J=7.3, H$_{ar}$), 6.16 (1H, m, H-2), 4.73 (1H, t, J=4.6, CHO$_2$), 3.94 (2H, m, 2H, CH$_2$O), 3.84 (1H, m, C-7), 3.83 (2H, m, CH$_2$O), 2.16 (2H, s, CH$_2$Ph), 0.89 (9H, s, $^t$BuSi), 0.06 (6H, s), 0.05 (6H, s).

EXAMPLE 13

Benzyl (3a,7,7a)-7-[(tert-butyldimethylsilyl)oxy)-3a-phenyl-3a,4,5,6,7,7a-hexahydro-1H-inden-3-yl]dimethylsilane (rac-13)

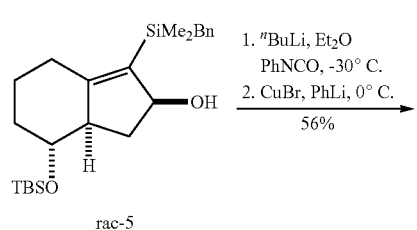

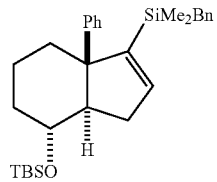

It is obtained by following the preparation of benzyl [(3a,7,7a)-7-(tert-butyldimethylsilyl)oxy)-3a-methyl-3a,4,5,6,7,7a-hexahydro-1H-inden-3-yl]dimethylsilane (rac-6) using rac-5 (0.101 g, 0.242 mmol), "BuLi (0.181 mL, 1.41 M, 0.255 mmol), PhNCO (0.029 mL, 0.266 mmol), CuBr (0.035 g, 0.242 mmol) and PhLi in dibutylether (0.133 mL, 2 M, 0.266 mmol) to give rac-13 [0.042 g, 56%, yellow oil]. $^1$H NMR (400 MHz, CDCl$_3$): δ=7.40 (2H, d, J=7.4, H$_{ar}$), 7.27 (2H, t, J=7.4, H$_{ar}$), 7.14 (1H, t, J=7.4, H$_{ar}$), 7.13 (2H, d, J=7.3, H$_{ar}$), 7.01 (1H, t, J=7.3, H$_{ar}$), 6.73 (2H, d, J=7.3, H$_{ar}$), 6.02 (1H, bs, H-2), 4.04 (1H, ddd, J$_1$=11.5, 9.5, 4.7, H-7), 1.89 (2H, s, CH$_2$Ph), 0.90 (9H, s, $^t$BuSi), 0.07 (3H, s), 0.03 (3H, s), −0.06 (3H, s), −0.12 (3H, s).

EXAMPLE 14

Benzyl (3a,7,7a)-7-[(tert-butyldimethylsilyl)oxy)-3a-p-tolyl-3a,4,5,6,7,7a-hexahydro-1H-inden-3-yl]dimethylsilane (rac-14)

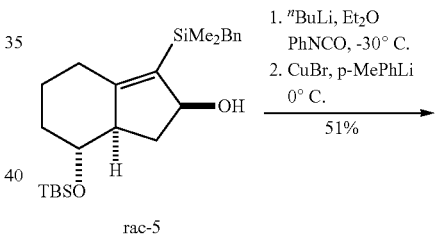

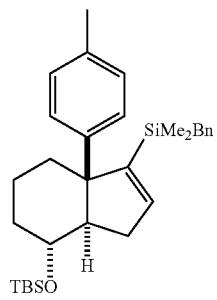

It is obtained by following the preparation of benzyl [(3a,7,7a)-7-(tert-butyldimethylsilyl)oxy)-3a-methyl-3a,4,5,6,7,7a-hexahydro-1H-inden-3-yl]dimethylsilane (rac-6) using rac-5 (0.116 g, 0.278 mmol), "BuLi (0.207 mL, 1.41 M, 0.292 mmol), PhNCO (0.033 mL, 0.306 mmol), CuBr (0.040 g, 0.278 mmol) and p-tolyllithium in Et$_2$O (0.927 mL, 0.33 M, 0.306 mmol) to give rac-14 [0.069 g, 51%, yellow oil]. $^1$H NMR (400 MHz, CDCl$_3$): δ=7.27 (2H, d, J=7.3, H$_{ar}$), 7.12 (2H, t, J=7.3, H$_{ar}$), 7.06 (2H, d, J=7.3, H$_{ar}$), 7.01 (1H, t, J=7.3, H$_{ar}$), 6.74 (2H, d, J=7.3, H$_{ar}$), 6.00 (1H, bs, H-2), 4.04 (1H, ddd, J=11.2, 9.3, 4.6, H-7), 2.29 (3H, s, MePh), 1.89 (2H, s, CH₂Ph), 0.89 (9H, s, ᵗBuSi), 0.06 (3H, s), 0.02 (3H, s), −0.06 (3H, s), −0.12 (3H, s).

EXAMPLE 15

(3a,4,7a)-4-(tert-Butyldimethylsilyloxy)-7a-methyl-octahydro-1H-inden-1-one (rac-15)

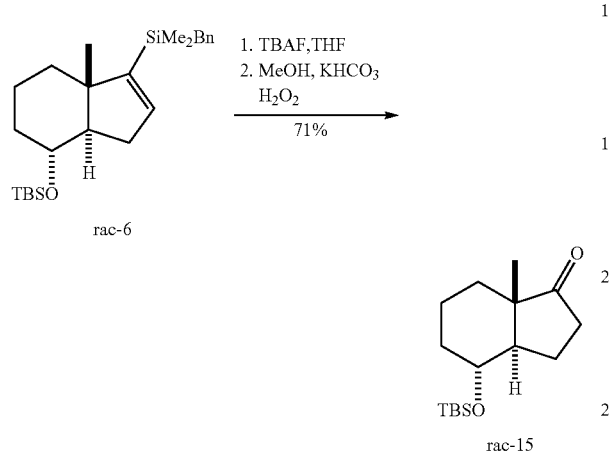

A solution of TBAF in THF (1.61 mL, 1M, 1.61 mmol) was added to a solution of rac-6 (0.318 g, 0.767 mmol) in THF (0.5 mL). MeOH (2 mL), KHCO₃ (0.153 g, 1.53 mmol) and H₂O₂ (1.60 mL, 30%) were added. After 48h a saturated solution of Na₂S₂O₃ was added. The resulting mixture was filtered. The organic phase was concentrated and purified by column chromatography (SiO₂, 1% ethyl acetate/hexane) to afford rac-15 [0.155 g, 71%, colorless oil]. ¹H NMR (250 MHz, CDCl₃): δ=3.70 (1H, td, J=10.5, 4.5, H-4), 2.42 (1H, m, H-3a), 0.88 (9H, s, ᵗBuSi), 0.86 (3H, s, H-8), 0.08 (6H, s, 2×CH₃Si).

EXAMPLE 16

(3a,4,7a)-4-(tert-Butyldimethylsilyloxy)-7a-trideuteromethyl octahydro-1H-inden-1-one (rac-16)

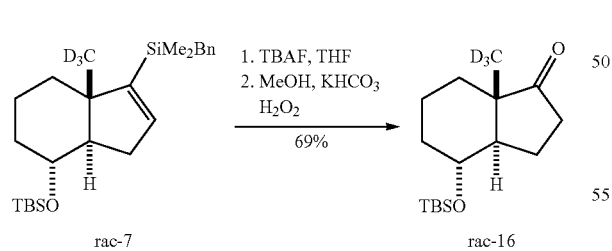

It is obtained by following the preparation of (3a,4,7a)-4-(tert-Butyldimethylsilyloxy)-7a-methyloctahydro-1H-inden-1-one (rac-15) using rac-7 (0.338 g, 0815 mmol), TBAF (1.79 ml, 1 M, 1.79 mmol), KHCO₃ (0.163 g, 1.63 mmol) and H₂O₂ (1.7 mL, 30%) and MeOH (2.16 mL) to give rac-16 [0.159 g, 69%, colorless oil]. ¹H NMR (250 MHz, CDCl₃): δ=3.70 (1H, td, J=10.5, 4.5, H-4), 2.42 (1H, m, H-3a), 0.88 (9H, s, ᵗBuSi), 0.08 (6H, s, 2×CH₃Si).

EXAMPLE 17

(3a,7,7a)-7-(tert-Butyldimethylsilyloxy)-3a-methyl-3a,4,5,6,7,7a-hexahydro-1H-inden-3-yl trifluoromethanesulfonate (rac-17)

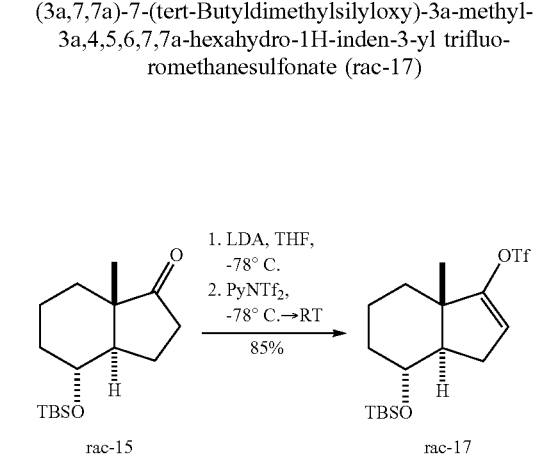

A solution of rac-15 (0.575 g, 2.04 mmol) in dry THF (5 mL) was added to solution of lithium diisopropyl amide (LDA) in THF (8.48 mL, 0.6M, 5.09 mmol) at −78° C. A solution of PyNTf₂ (1.312 g, 3.663 mmol) dissolved in THF (5 mL) was added. The mixture was allowed to reach RT and was filtered under vacuum. The organic phase was concentrated and purified by flash chromatography (SiO₂, 0.5% methyl tert-butylether/hexanes) affording rac-17 [0.719 g, 85%, colorless oil]. ¹H-NMR (250 MHz, CDCl₃): δ=5.58 (1H, m, H-2), 3.73 (1H, td, J=10.5, 4.5, H-7), 0.98 (3H, s, H-8), 0.88 (9H, s, ᵗBuSi), 0.05 (6H, s, 2×CH₃Si).

EXAMPLE 18

(3a,7,7a)-7-(tert-Butyldimethylsilyloxy)-3a-trideuteromethyl-3a,4,5,6,7,7a-hexahydro-1H-inden-3-yl trifluoromethanesulfonate (rac-18)

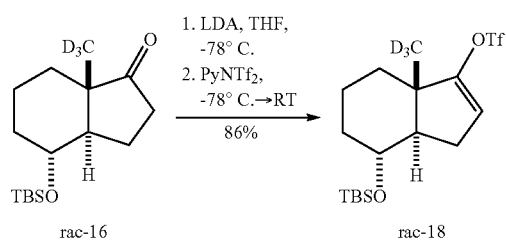 [SMILES: [2H]C([2H])([2H])[C@]12CCC[C@@H](O[Si](C)(C)C(C)(C)C)[C@@H]1CCC2=O ; [2H]C([2H])([2H])[C@]12CCC[C@@H](O[Si](C)(C)C(C)(C)C)[C@@H]1CC=C2OS(=O)(=O)C(F)(F)F]

It is obtained by following the preparation of (3a,4,7a)-7-(tert-butyldimethylsilyloxy)-3a-methyl-3a,4,5,6,7,7a-hexahydro-1H-inden-3-yl trifluoromethanesulfonate (rac-17) using rac-16 (0.131 g, 2.04 mmol), LDA (2.8 mL, 0.5 M, 1.4 mmol), PyNTf₂ (0.328 g, 0.835 mmol) to give rac-18 [0.165 g, 85%, R_f=0.76 (8% ethyl acetate/hexanes), colorless oil]. ¹H-NMR (250 MHz, CDCl₃): δ=5.58 (1H, m, H-2), 3.72 (1H, td, J=10.5, 4.5, H-7), 0.89 (9H, s, ᵗBuSi), 0.06 (6H, s, 2×CH₃Si).

EXAMPLE 19

Ethyl (E)-3-(4,4,5,5-tetramethyl-1,3,2-dioxaborolan-2-yl)but-2-enoate (19)

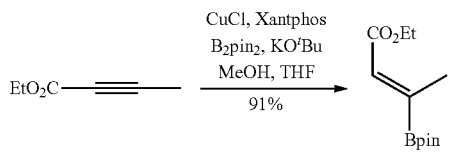

KOtBu (0.091 mL, 1.7 M, 0.154 mmol) and Xantphos (0.045 g, 0.077 mmol) were added to a suspension of CuCl (0.008 g, 0.077 mmol) in THF (2.5 mL). B$_2$pin$_2$ (0.718 g, 2.826 mmol) was added. A solution of Ethyl 2-butynoate (0.288 g, 2.57 mmol) in THF (1 mL) and MeOH (0.1 mL) was added. The mixture was filtered, concentrated and purified by flash chromatography (SiO$_2$, 2% ethyl acetate/hexanes) to afford 19 [0.562 g, 91%, colorless liquid]. $^1$H-NMR (250 MHz, CDCl$_3$): δ=6.41 (1H, s, H-2), 4.13 (2H, q, J=7.1, OC$\underline{H_2}$CH$_3$), 2.13 (3H, t, J=7.1, OCH$_2$C$\underline{H_3}$), 1.23 (15H, s).

EXAMPLE 20

Ethyl (E)-3-((3a',7',7a')-7'-((tert-butyldimethylsilyl)oxy)-3a'-trideuteromethyl-3a',4',5',6',7',7a'-hexahydro-1H-inden-3'-yl)but-2-enoate (rac-20)

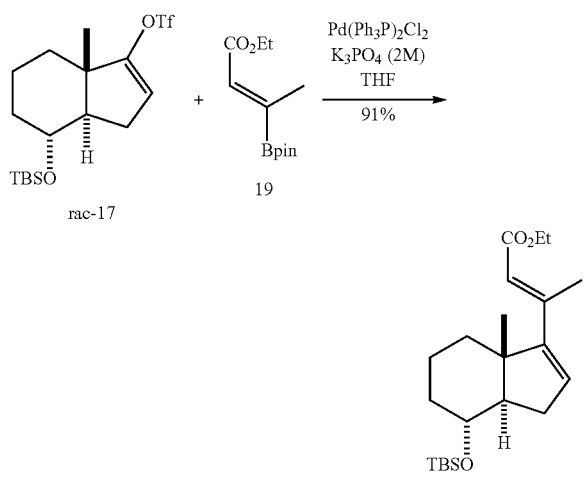

A solution of rac-17 (0.338 g, 0.815 mmol) and 19 (0.294 g, 1.22 mmol) in THF (13 mL) was treated with K$_3$PO$_4$ (10.7 mL, 2 M, 21.4 mmol) and (Ph$_3$P)$_2$PdCl$_2$ (0.028 g, 0.04 mmol). The reaction mixture was stirred at RT and a saturated solution of NH$_4$Cl (15 mL) was added. The aqueous phase was extracted with methyl tert-butylether. The organic phase was concentrated and purified by flash chromatography (SiO$_2$, 0.5% methyl tert-butylether/hexanes) to afford rac-20 [0.279 g, 91%, colorless liquid]. $^1$H-NMR (250 MHz, CDCl$_3$): δ=6.11 (1H, m, H-2'), 5.86 (1H, s, H-2), 4.14 (2H, q, J=7.1, OC$\underline{H_2}$CH$_3$), 3.75 (1H, td, J=10.4, 5.3, H-7), 2.35 (1H, m), 2.29 (3H, s, H-4), 1.27 (3H, t, J=7.1, OCH$_2$C$\underline{H_3}$), 0.96 (3H, s, H-8'), 0.88 (9H, $^t$BuSi), 0.05 (6H, s, 2×CH$_3$Si).

EXAMPLE 21

Ethyl (E)-3-((3a',7',7a')-7'-((tert-butyldimethylsilyl)oxy)-3a'-trideuteromethyl-3a',4',5',6',7',7a'-hexahydro-1H-inden-3'-yl)but-2-enoate (rac-21)

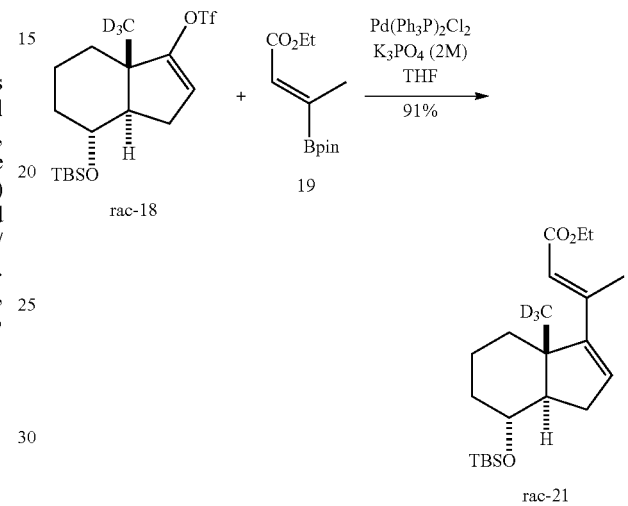

It is obtained by following the preparation of ethyl (E)-3-((3a'7',7a')-7a'-((tert-butyldimethylsilyl)oxy)-3a'-methyl-3a',4',5',6',7',7a'-hexahydro-1H-inden-3'-yl)but-2-enoate (rac-20) using rac-18 (0.210 g, 0.554 mmol), 19 (0.160 g, 0.665 mmol), K$_3$PO$_4$ (7.27 mL, 2 M, 14.54 mmol) and (Ph$_3$P)$_2$PdCl$_2$ (0.019 g, 0.028 mmol) to give rac-21 [0.191 g, 91%, colorless liquid]. $^1$H-NMR (250 MHz, CDCl$_3$): δ=6.11 (1H, m, H-2'), 5.86 (1H, s, H-2), 4.14 (2H, q, J=7.1, OC$\underline{H_2}$CH$_3$), 3.75 (1H, td, J=10.4, 5.3, H-7), 2.35 (1H, m), 2.29 (3H, s, H-4), 1.26 (3H, t, J=7.1, OCH$_2$C$\underline{H_3}$), 0.87 (9H, s, $^t$BuSi), 0.04 (6H, s, CH$_3$Si).

EXAMPLE 22

(R)-Ethyl 3-((3a',7',7a')-7'-(tert-butyldimethylsilyloxy)-3a'-methyl-3a',4',5',6',7',7a'-hexahydro-1H-inden-3'-yl)butanoate (rac-22)

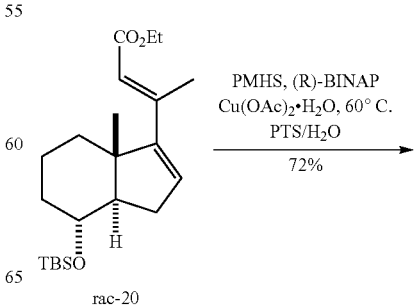

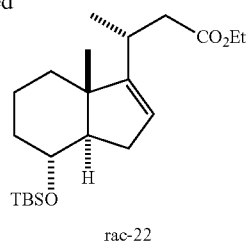

A solution of rac-20 (0.038 g, 0.10 mmol) in polyoxyethenyl-alfa-tocoferyl sebacate/H$_2$O (2%, 1.5 mL) was sonicated, (R)-BINAP (0.007 g, 0.01 mmol), Cu(OAc)$_2$ (0.002g, 0.01 mmol) and poly(methylhydrosiloxane) (PMHS) (0.096 g, 1.60 mmol) were added: The reaction mixture underwent ultrasound action and heated at 60° C. After 48 h the reaction was quenched by the addition of aqueous solution of NH$_4$F. The resulting mixture was concentrated and purified by flash chromatography (SiO$_2$, 2% ethyl acetate/hexanes) to afford rac-22 [0.027 g, 72%, yellow oil]. $^1$H-NMR (250 MHz, CDCl$_3$): δ=6.11 (1H, m, H-2'), 4.09 (2H, q, OC$\underline{H_2}$CH$_3$), 3.73 (1H, td, J=10.4, 4.4, H-7'), 2.5 (1H, dd, H-2), 2.35 (1H, dd, H-2), 1.23 (3H, t, J=7.2, OCH$_2$C$\underline{H_3}$), 1.04 (3H, d, J=6.7, H-4), 0.87 (9H, $^t$BuSi), 0.76 (3H, s, H-8'), 0.04 (6H, s, 2×CH$_3$Si).

EXAMPLE 23

(S)-Ethyl 3-((3a',7',7a')-7'-(tert-butyldimethylsilyl) oxy)-3a'-methyl-3a',4',5',6',7',7a'-hexahydro-1H-inden-3'-yl)butanoate (rac-23)

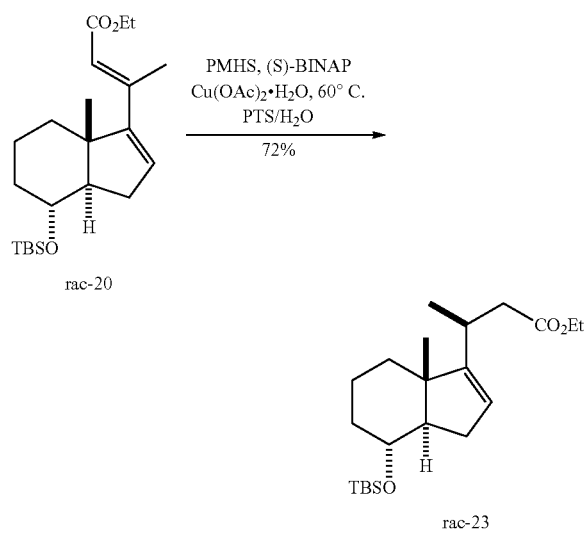

It is obtained by following the preparation of (R)-ethyl 3-((3a',7',7a')-7'-(tert-butyldimethylsilyloxy)-3a'-methyl-3a',4',5',6',7',7a'-hexahydro-1H-inden-3'-yl)butanoate (rac-22) using rac-20 (0.038g, 0.10 mmol), (S)-BINAP (0.007 g, 0.01 mmol), Cu(OAc)$_2$ (0.002 g, 0.01 mmol), (PMHS) (0.096 g, 1.60 mmol) and NH$_4$F (0.5 mL) to give rac-23 (0.027 g, 72%, yellow oil). $^1$H-NMR (250 MHz, CDCl$_3$): δ=5.39 (1H, m, H-2'), 4.11 (2H, q, J=7.1, OC$\underline{H_2}$CH$_3$), 3.76 (1H, td, J=10.7, 5.3, H-7'), 2.20 (1H, m, H-7a'), 1.25 (3H, t, J=7.2, OCH$_2$C$\underline{H_3}$), 1.11 (3H, d, J=6.9, H-4), 0.88 (9H, s, $^t$BuSi), 0.81 (3H, s, H-8'), 0.05 (6H, s, 2×CH$_3$Si).

EXAMPLE 24

(R)-Ethyl 3-((3a',7',7a')-7'-(tert-butyldimethylsilyloxy)-3a'-trideuteromethyl-3a',4',5',6',7',7a'-hexahydro-1H-inden-3'-yl)butanoate (rac-24)

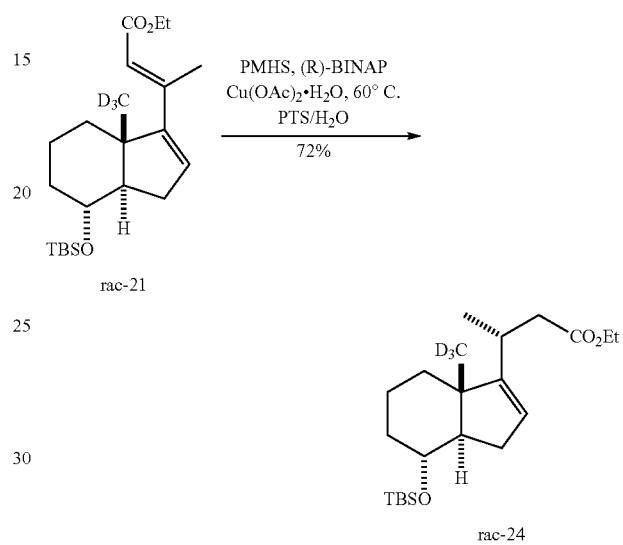

It is obtained by following the preparation of (R)-ethyl 3-((3a',7',7a')-7'-(tert-butyldimethylsilyloxy)-3a'-methyl-3a',4',5',6',7',7a'-hexahydro-1H-inden-3'-yl)butanoate (rac-22) using rac-21 (0.055g, 0.145 mmol), (R)-BINAP (0.010 g, 0.015 mmol), Cu(OAc)$_2$ (0.003 g, 0.015 mmol), (PMHS) (0.070 g, 1.16 mmol) and NH$_4$F (0.5 mL) to give rac-24 [0.040 g, 72%, yellow oil]. $^1$H-NMR (250 MHz, CDCl$_3$): δ=6.11 (1H, m, H-2'), 4.09 (2H, m, OC$\underline{H_2}$CH$_3$), 3.73 (1H, td, J=10.4, 4.4, H-7'), 2.5 (1H, m, H-2), 2.35 (1H, m, H-2), 1.22 (3H, t, J=7.2, OCH$_2$C$\underline{H_3}$), 1.06 (3H, d, J=6.7, H-4), 0.87 (9H, s, $^t$BuSi), 0.04 (6H, s, 2×CH$_3$Si).

EXAMPLE 25

(R)-3-((3a',7',7a')-7'-(tert-Butyldimethylsilyloxy)-3a'-methyl-3a',4',5',6',7',7a'-hexahydro-1H-inden-3'-yl)butan-1-ol (rac-25)

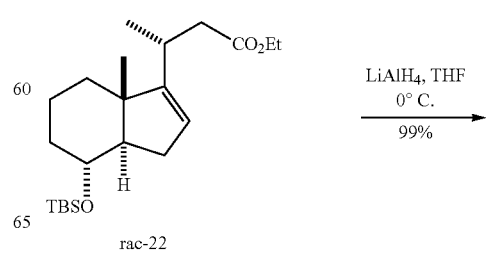

-continued

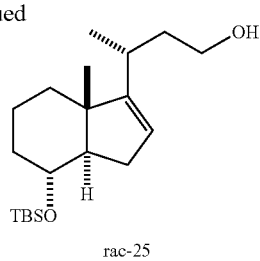

rac-25

Lithium aluminium hydride (LiAlH₄) (0.033 g, 0.857 mmol) was added to a solution of rac-22 (0.163 g, 0.428 mmol) in THF (2 mL) at 0° C. The reaction mixture was allowed to warm to RT. The mixture was cooled to 0° C. and then H₂O and HCl (10%) were added. The aqueous phase was extracted with methyl tert-butylether (25 mL), it was concentrated and purified by flash chromatography (SiO₂, 4% ethyl acetate/hexanes) to afford rac-25 [0.143 g, 99%, white solid]. ¹H-NMR (250 MHz, CDCl₃): δ=5.31 (1H, m, H-2'), 3.74 (1H, td, J=10.4, 4.6, H-7'), 3.60 (2H, td, J=6.7, 2.8, H-1), 1.01 (3H, d, J=6.9, H-4), 0.87 (9H, s, ʹBuSi), 0.76 (3H, s, H-8'), 0.04 (6H, s, 2×CH₃Si).

EXAMPLE 26

(R)-3-((3a',7',7a')-7'-(tert-Butyldimethylsilyloxy)-3a'-trideuteromethyl-3a',4',5',6',7',7a'-hexahydro-1H-inden-3'-yl)butan-1-ol (rac-26)

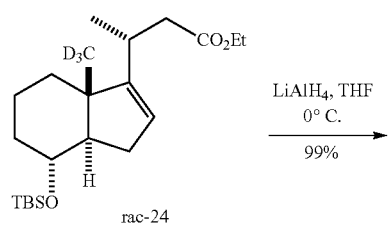

rac-24

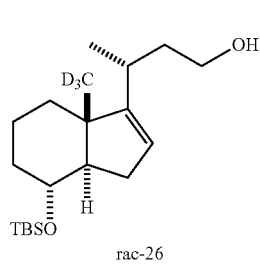

rac-26

It is obtained by following the preparation of (R)-3-((3a',7',7a')-7'-((tert-butyldimethylsilyl)oxy)-3a'-methyl-3a',4',5',6',7',7a'-hexahydro-1H-inden-3'-yl)butan-1-ol (rac-25) using rac-24 (0.438 g, 1.15 mmol) and LiAlH₄ (0.087 g, 2.30 mmol) to give rac-26 [0.143 g, 99%, white solid]. ¹H-NMR (250 MHz, CDCl₃): δ=5.31 (1H, m, H-2'), 3.74 (1H, td, J=10.4, 4.6, H-7'), 3.60 (2H, td, J=6.7, 2.8, H-1), 1.02 (3H, d, J=6.9, H-4), 0.88 (9H, s, ʹBuSi), 0.05 (6H, s, 2×CH₃Si).

EXAMPLE 27

(R)-3-((1',3a',4',7a')-4'-((tert-Butyldimethylsilyl)oxy)-7a'-methyloctahydro-1H-inden-1'-yl)butan-1-ol (rac-27)

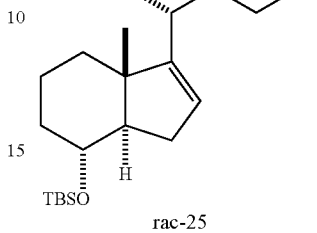

rac-25

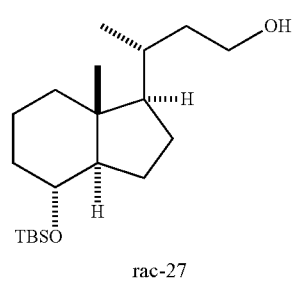

rac-27

Pd/C (0.010 g, 10%) was added to a solution of rac-25 (0.104 g, 0.307 mmol) in ethyl acetate (6 mL). The reaction was stirred under H₂ pressure. The mixture was filtered, concentrated and purified by flash chromatography (SiO₂, 6% ethyl acetate/hexanes) to afford rac-27 [0.0.96 g, 91%, yellow oil]. ¹H-NMR (250 MHz, CDCl₃): δ=3.59 (3H, m, H-7', H-1), 0.92 (3H, d, J=6.9, C-4), 0.86 (9H, s, ʹBuSi), 0.66 (3H, s, H-8'), 0.00 (6H, s, 2×CH₃Si).

EXAMPLE 28

(R)-3-((1',3a',4',7a')-4'-((tert-Butyldimethylsilyl)oxy)-7a'-trideuteromethyloctahydro-1H-inden-1'-yl)butan-1-ol (rac-28)

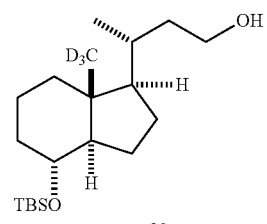

rac-28

It is obtained by following the preparation of (R)-3-((1',3a',4',7a')-4'-((tert-butyldimethylsilyl)oxy)-7a'-methyl-octhydro-1H-inden-1'-yl)butan-1-ol (rac-27) using rac-26 (0.127 g, 0.375 mmol), Pd/C (0.010 g, 10%) to give rac-28 [0.115 g, 90%, yellow oil]. $^1$H-NMR (250 MHz, CDCl$_3$): δ=3.59 (3H, m, H-7', H-1), 0.91 (3H, d, J=6.9, C-4), 0.87 (9H, s, $^t$BuSi), 0.01 (6H, s, 2×CH$_3$Si).

EXAMPLE 29 tert-Butyl [((1',3a',4',7a')-1-(R)-4-iodobutan-2-yl)-7a'-methyloctahydro-1H-inden-4-yloxy)dimethylsilane (rac-29)

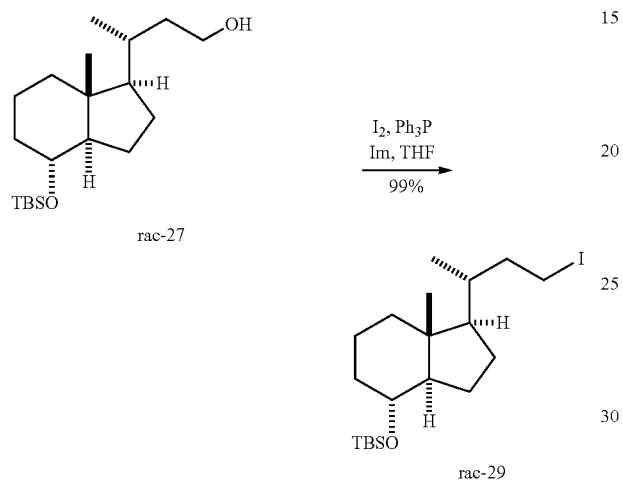

Triphenyl phosphine (Ph$_3$P) (0.084 g, 0.321 mmol), imidazole (0.035 g, 0.507 mmol) and I$_2$ (0.081 g, 0.321 mmol) were added to a solution of rac-27 (0.091 g, 0.267 mmol) in THF (5 mL). The mixture was stirred at RT, a few drops of NaHCO$_3$ and Na$_2$S$_2$O$_3$ were added. Then a saturated aqueous solution of NaHCO$_3$ and Na$_2$S$_2$O$_3$ was added. The aqueous phase was extracted with methyl tert-butylether. The organic phase was concentrated and purified by flash chromatography (SiO$_2$, 1% methyl tert-butylether/hexanes) to afford rac-29 [0.120 g, 99%, colorless oil]. $^1$H-NMR (250 MHz): 3.55 (1H, td, J=9.7, 4.2, C-7'), 3.30 (1H, td, J=9.5, 4.8, C-1), 3.10 (1H, m, H-7a'), 0.90 (3H, d, J=6.9, C-4), 0.88 (9H, s, $^t$BuSi), 0.68 (3H, s, C-8'), 0.04 (6H, s, 2×CH$_3$Si).

EXAMPLE 30 tert-Butyl [((1',3a',4',7a')-1-((R)-4-iodobutan-2-yl)-7a'-trideuteromethyloctahydro-1H-inden-4-yloxy) dimethylsilane (rac-30)

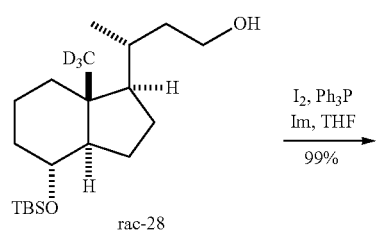

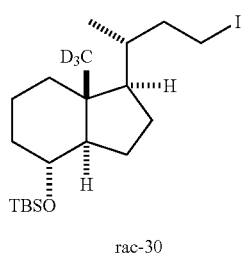

It is obtained by following the preparation of tert-butyl [((1',3a',4',7a')-1-((R)-4-iodobutan-2-yl)-7a'-methyloctahydro-1H-inden-4-yloxy)dimethylsilane (rac-29) using rac-28 (0.100 g, 0.294 mmol), Ph$_3$P (0.092 g, 0.352 mmol), imidazol (0.038 g, 0.559 mmol) and I$_2$ (0.089 g, 0.352 mmol) to give rac-30 (0.131 g, 99%, colorless oil]. $^1$H-NMR (250 MHz): 3.55 (1H, td, J=9.7, 4.2, H-7'), 3.30 (1H, td, J=9.5, 4.8, H-1), 3.10 (1H, m, H-1), 2.05 (1H, m, H-7a'), 0.89 (3H, d, J=6.9, H-4), 0.87 (9H, s, $^t$BuSi), 0.03 (6H, s, 2×CH$_3$Si).

EXAMPLE 31 tert-Butyl 5-(R)-[((1',3a',4',7a')-4'-(tert-butyldimethylsilyloxy)-7a'-methyloctahydro-1H-inden-1'-yl) hexanoate (rac-31)

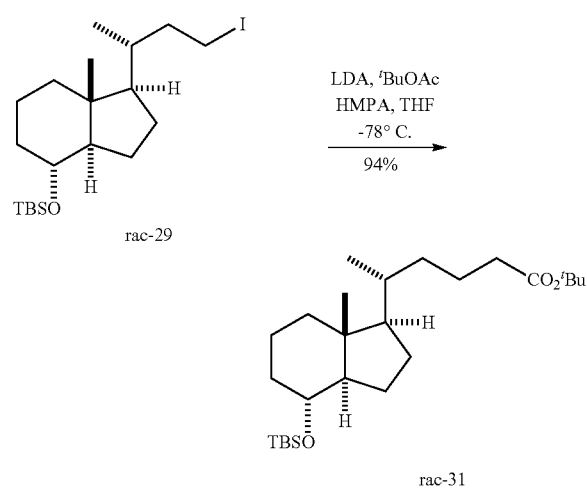

Hexamethylphosphoramide (0.058 mL, 0.333 mmol) was added to a solution of LDA in THF (0.67 mL, 0.5 M, 0.333 mmol) at −78° C., and $^t$BuOAc (0.045 mL, 0.333 mmol) was added and then a solution of rac-29 (0.050 g, 0.111 mmol) in THF (3 mL) was added. After stirring for 30 min a saturated aqueous solution of NH$_4$Cl was added at −78° C. The aqueous phase was extracted with MTBE, it was concentrated and purified by flash chromatography (SiO$_2$, 1% ethyl acetate/hexanes) to afford rac-31 [0.046 g, 94%, white solid]. $^1$H-NMR (250 MHz, CDCl$_3$): δ=3.52 (1H, td, J=9.8, 4.4, H-7'), 2.16 (2H, td, J=7.6, 3.0, H-2), 1.43 (9H, s, $^t$BuO), 0.90 (3H, d, J=6.5, H-5), 0.88 (9H, s, $^t$BuSi), 0.65 (3H, s, H-8'), 0.03 (6H, s, 2×CH$_3$Si).

EXAMPLE 32 tert-Butyl 5-(R)-[((1',3a',4',7a')-4'-(tert-butyldimethylsilyloxy)-7a'-trideuteromethyloctahydro-1H-inden-1'-yl)hexanoate (rac-32)

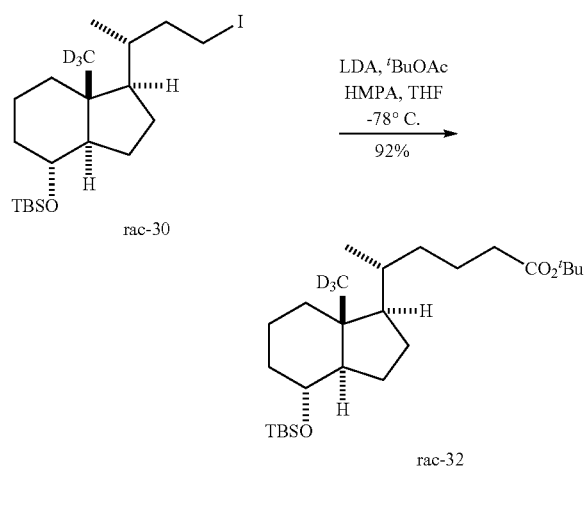

It is obtained by following the preparation of tert-butyl 5-(R)-[((1',3a',4',7a')-4'-(tert-butyldimethylsilyloxy)-7a'-methyloctahydro-1H-inden-1'-yl)hexanoate (rac-31) using rac-30 (0.120 g, 0.266 mmol) HMPA (0.139 mL, 0.799 mmol), LDA (1.6 mL, 0.5 M, 0.80 mmol) and $^t$BuOAc (0.107 mL, 0.799 mmol) to give rac-32 [0.108 g, 92%, white solid]. $^1$H-NMR (250 MHz, CDCl$_3$): δ=3.52 (1H, td, J=9.8, 4.4, H-7'), 2.16 (2H, td, J=7.6, 3.0, H-2), 1.43 (9H, s, $^t$BuO), 0.90 (3H, d, J=6.5, H-5), 0.87 (9H, s, $^t$BuSi), 0.04 (6H, s, 2×CH$_3$Si).

EXAMPLE 33

(S)-3-((3a',7',7a')-7'-(tert-Butyldimethylsilyloxy)-3a'-methyl-3a',4',5',6',7',7a'-hexahydro-1H-inden-3'-yl)butan-1-ol (rac-33)

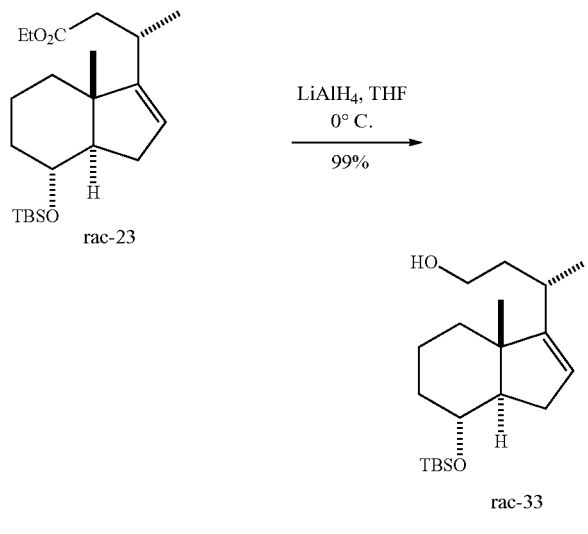

It is obtained by following the preparation of (R)-3-((3a', 7',7a')-7'-(tert-butyldimethylsilyloxy)-3a'-methyl-3a',4',5',6', 7',7a'-hexahydro-1H-inden-3'-yl)butan-1-ol (rac-25) using rac-23 (0.163 g, 0.428 mmol) and LiAlH$_4$ (0.033 g, 0.857 mmol) to give rac-33 [0.143 g, 99%, white solid]. $^1$H-NMR (250 MHz, CDCl$_3$): δ=5.39 (1H, m, H-2'), 3.75 (1H, td, J=10.4, 4.5, H-7'), 3.63 (2H, m, H-1), 1.10 (3H, d, J=6.9, H-4), 0.88 (9H, s, $^t$BuSi), 0.79 (3H, s, H-8'), 0.05 (6H, s, 2×CH$_3$Si).

EXAMPLE 34 tert-Butyl ((3a',7',7a')-3'-((S)-4-iodobutan-2-yl)-3a'-methyl-3a',4',5',6',7',7a'-hexahydro-1H-inden-7'-yloxy)dimethylsilane (rac-34)

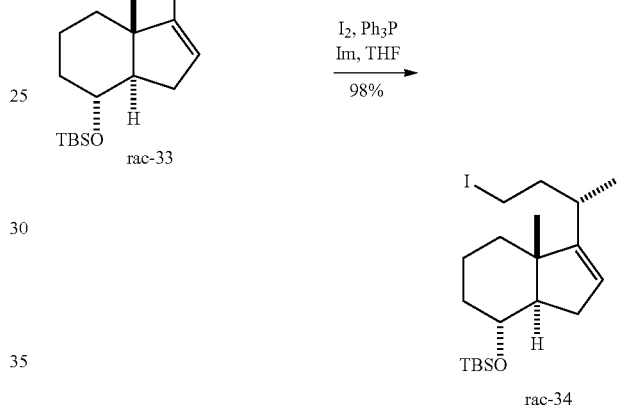

It is obtained by following the preparation of tert-butyl [((1',3a',4',7a')-1-((R)-4-iodobutan-2-yl)-7a'-methyloctahydro-1H-inden-4-yloxy)dimethylsilane (rac-29) using rac-33 (0.091 g, 0.267 mmol), Ph$_3$P (0.084 g, 0.321 mmol), imidazole (0.035 g, 0.507 mmol) and I$_2$ (0.081 g, 0.321 mmol) to give rac-34 [0.117 g, 98%, colorless oil]. $^1$H-NMR (250 MHz): δ=5.37 (1H, m, H-2'), 3.75 (1H, td, J=10.4, 4.5, H-7'), 3.14 (2H, t, J=7.4, H-1), 1.07 (3H, d, J=6.9, H-4), 0.89 (9H, s, $^t$BuSi), 0.80 (3H, s, H-3a'), 0.05 (6H, s, 2×Ch$_3$Si).

EXAMPLE 35 tert-Butyl 5-(S)-[((3a',7',7a')-7'-(tert-butyldimethylsilyloxy)-3a'-methyl-3a',4',5',6',7',7a'-hexahydro-1H-inden-3'-yl)hexanoate (rac-35)

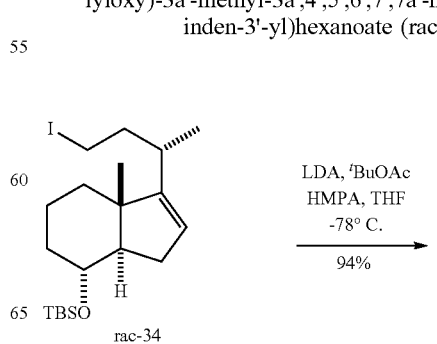

-continued

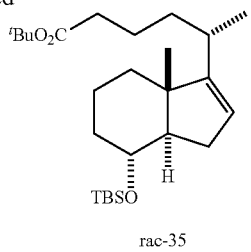

rac-35

It is obtained by following the preparation of tert-butyl 5-(R)-[((1',3a',4',7a')-4'-(tert-butyldimethylsilyloxy)-7a'-methyloctahydro-1H-inden-1'-yl)hexanoate (rac-31) using rac-34 (0.050 g, 0.111 mmol), HMPA (0.058 mL, 0.333 mmol), LDA (0.67 mL, 0.5 M, 0.333 mmol) and $^t$BuOAc (0.045 mL, 0.333 mmol) to give rac-35 [0.046 g, 94%, white solid]. $^1$H-NMR (250 MHz, CDCl$_3$): δ=5.31 (1H, m, H-2'), 3.73 (1H, td, J=10.4, 4.5, H-7'), 2.16 (2H, t, J=7.1, H-2), 1.43 (9H, s, $^t$BuO), 1.05 (3H, d, J=6.7, H-6), 0.88 (9H, s, $^t$BuSi), 0.77 (3H, s, H-3a'), 0.04 (6H, s, 2×Ch$_3$Si).

EXAMPLE 36 tert-Butyl 5-(R)-[(1',3a',4',7a')-4'-hydroxy-7a'-methyloctahydro-1H-inden-1'-yl)hexanoate (rac-36)

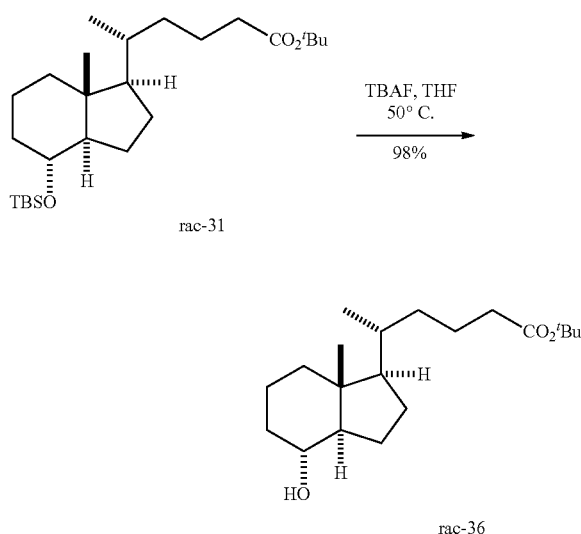

A solution of Tetrabutylammonium fluoride (TBAF) in THF (0.530 mL, 1M, 0.530 mmol) was added to a solution of rac-31 (0.155 g, 0.353 mmol) in THF (5 mL). After stirring for 7 h, NH$_4$Cl was added. The aqueous layer was extracted with MTBE, it was concentrated and purified by flash chromatography (SiO$_2$, 8% ethyl acetate/hexanes) to afford rac-36 [0.143 g, 98%, yellow oil]. $^1$H-NMR (250 MHz, CDCl$_3$): δ=3.53 (1H, td, J=10.3, 5.1, H-7'), 2.14 (2H, td, J=7.5, 3.8, H-2), 1.70 (9H, m), 1.42 (9H, s, $^t$BuO), 1.15 (8H, m), 0.89 (3H, d, J=6.4, H-5), 0.64 (3H, s, H-8').

EXAMPLE 37 tert-Butyl 5-(R)-[(1',3a',4',7a')-4'-hydroxy-7a'-trideuteromethyloctahydro-1H-inden-1'-yl)hexanoate (rac-37).

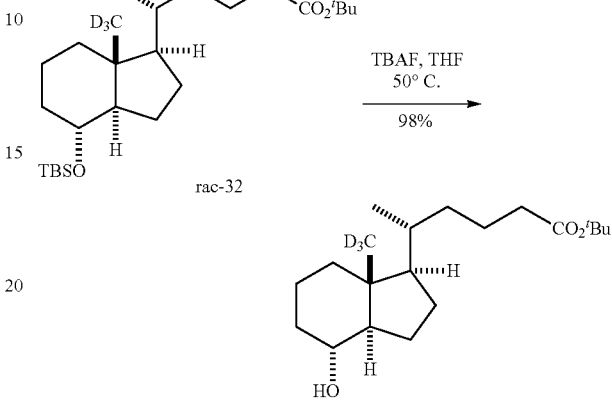

It is obtained by following the preparation of tert-butyl 5-(R)-[((1',3a',4',7a')-4'-hydroxy-7a'-methyloctahydro-1H-inden-1'-yl)hexanoate (rac-36) using rac-32 (0.202 g, 0.460 mmol) and TBAF (0.691 mL, 1M, 0.691 mmol) to give rac-37 [0.146 g, 98%, yellow oil]. $^1$H-NMR (250 MHz, CDCl$_3$): δ=3.53 (1H, td, J=10.3, 5.1, H-7'), 2.14 (2H, td, J=7.5, 3.8, H-2), 1.70 (9H, m), 1.42 (9H, s, $^t$BuO), 1.16 (8H, m), 0.88 (3H, d, J=6.4, H-5).

EXAMPLE 38 tert-Butyl 5-(R)-[(1',3a',7a')-7a'-methyl-4'-oxooctahydro-1H-inden-1'-yl)hexanoate (rac-38)

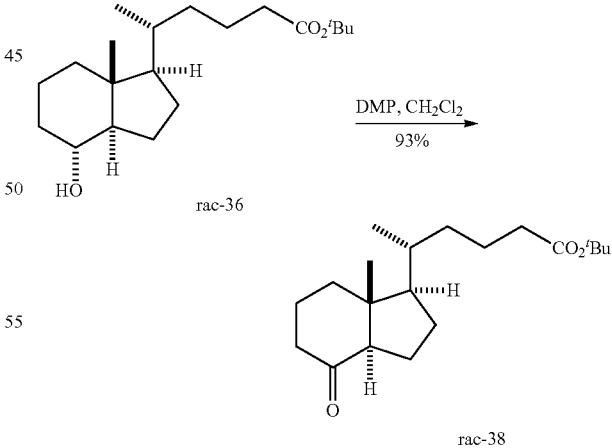

Dess-Martin periodinane (0.579 g, 1.540 mmol) was added to a solution of rac-36 (0.155 g, 0.353 mmol) in CH$_2$Cl$_2$ (2 mL). The reaction was filtered, concentrated and purified by flash chromatography (SiO$_2$, 3% ethyl acetate/hexanes) to afford rac-38 [0.084 g, 93%, yellow oil]. $^1$H-NMR (250 MHz, CDCl$_3$): δ=2.44 (1H, 2d, J=11.7, 7.5, H-7'), 2.19 (5H, m), 1.80 (13H, m), 1.44 (9H, s, ⁱBuO), 0.96 (3H, d, J=5.7, H-5), 0.63 (3H, s, H-8').

EXAMPLE 39 tert-Butyl 5-(R)-[(1',3a',7a')-7a'-trideuteromethyl-4'-oxooctahydro-1H-inden-1'-yl)hexanoate (rac-39)

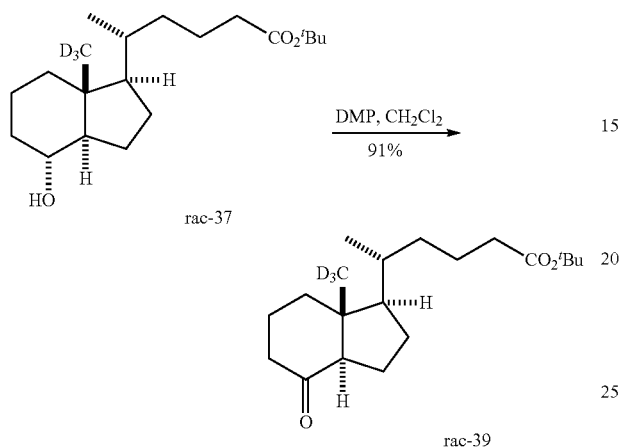

It is obtained by following the preparation of tert-butyl 5-(R)-[((1',3a',7a')- 7a'-methyl-4'-oxooctahydro-1H-inden-1'-yl)hexanoate (rac-38) using rac-37 (0.165 g, 0.508 mmol), DMP (0.323 g, 0.762 mmol) to give rac-39 [0.149 g, 91%, yellow oil]. ¹H-NMR (250 MHz, CDCl₃): δ=2.44 (1H, 2d, J=11.7, 7.5, H-7'), 2.19 (5H, m), 1.80 (13H, m), 1.44 (9H, s, ⁱBuO), 0.95 (3H, d, J=5.7, H-5).

EXAMPLE 40 tert-Butyl 5-(R)-[(1',3a',7a',E)-4-(bromomethylen)-7a'-methyloctahydro-1H-inden-1'-yl)hexanoate (rac-40)

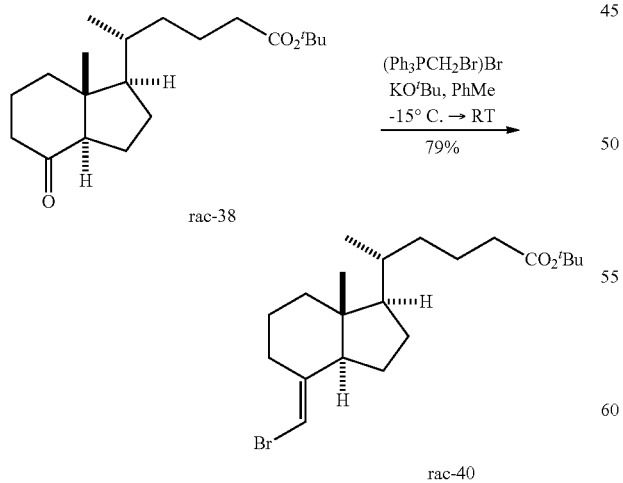

A suspension of (Ph₃PCH₂Br)Br (2.83 g, 6.49 mmol) in toluene (20 mL) was prepared by sonication. A solution of KOⁱBu (3.76 mL, 6.38 mmol, 1.7M) was added to the suspension cooled at -15° C. After stirring a solution of rac-38 (0.349 g, 1.08 mmol) in toluene (15 mL) was added. The resulting mixture was stirred at −15° C. and at RT. The reaction was quenched by addition of saturated solution of NH₄Cl and the mixture was filtered. The filtrate was concentrated and purified by flash chromatography (SiO₂, hexanes) to afford rac-40 [0.340 g, 79%, yellow oil]. ¹H-NMR (400 MHz, CDCl₃): δ=5.63 (1H, s, H-4'), 2.85 (1H, m, H-5'), 2.16 (2H, m, H-2), 1.44 (9H, s, ⁱBuO), 0.93 (3H, d, J=5.8, H-6), 0.63 (3H, s, H-7a').

EXAMPLE 41 tert-Butyl 5-(R)-[(1',3a',7a',E)-4-(bromomethylen)-7a'-trideuteromethyloctahydro-1H-inden-1'-yl) hexanoate (rac-41)

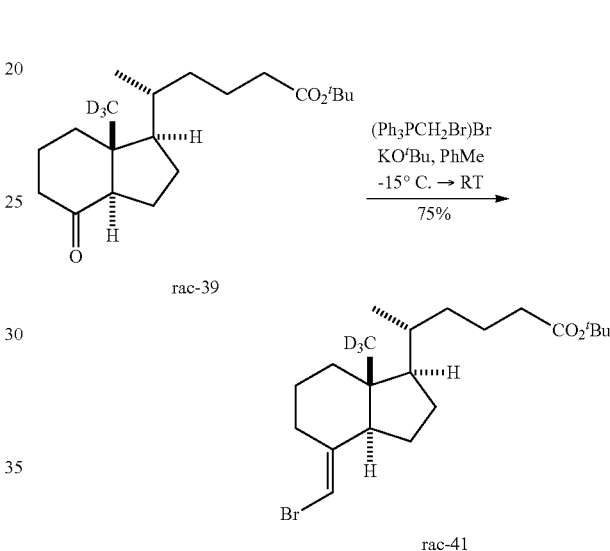

It is obtained by following the preparation of tert-butyl 5-(R)-[(1',3a',7a',E)-4-(bromomethylen)-7a'-methyloctahydro-1H-inden-1'-yl)hexanoate (rac-40). using rac-39 (0.077 g, 0.239 mmol), (Ph₃PCH₂Br)Br (0.625 g, 1.43 mmol) and KOⁱBu (0.83 mL, 1.49 mmol, 1.7M) to give rac-41 [0.071 g, 75%, yellow oil]. ¹H-NMR (400 MHz, CDCl₃): δ=5.63 (1H, s, H-4'), 2.85 (1H, m, H-5'), 2.16 (2H, m, H-2), 1.44 (9H, s, ⁱBuO), 0.92 (3H, d, J=5.8, H-6).

EXAMPLE 42 tert-Butyl 5-(R)-[(1',3a',7a',E)- 7a'-methyl-4'-((4,4,5,5-tetramethyl-1,3,2-dioxaboralan-2-yl)methylen) octahydro-1H-inden-1'-yl)hexanoate (rac-42)

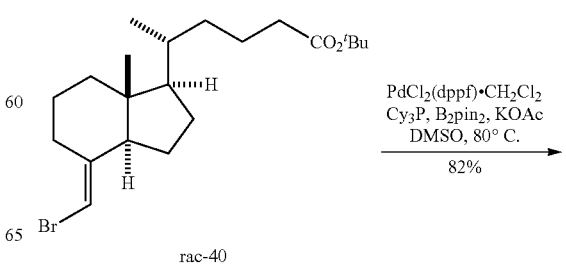

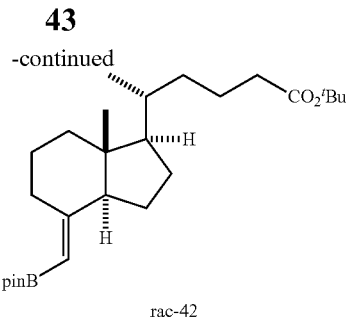

rac-42

Tricyclohexylphosphine (Cy₃P) (2 mg, 0.007 mmol) and Pd(dppf)Cl₂.CH₂Cl₂ (3 mg, 0.004 mmol) were dissolved in DMSO (1 mL). A solution of rac-40 (0.049 g, 0.123 mmol) in DMSO (1.5 mL) was added. KOAc (0.036 g, 0.369 mmol) and Bis(pinacolato)diboron (Pin₂B₂) (0.062 g, 0.246 mmol) were added. The mixture was heated at 80° C. The reaction was quenched by addition of H₂O and extracted with MTBE. The organic phase was concentrated and purified by flash chromatography (SiO₂, 1-2% ethyl acetate/hexanes) to afford rac-42 [0.045 g, 82%, yellow oil]. ¹H-NMR (400 MHz, CDCl₃): δ=4.89 (1H, s, H-4'), 3.15 (1H, m, H-5'), 2.16 (2H, m, H-2), 1.43 (9H, s, ᵗBuO), 1.25 (12H, s, CH₃-pinacol), 0.92 (3H, d, J=6.1, H-6), 0.53 (3H, s, H-7a').

EXAMPLE 43 tert-Butyl 5-(R)-[(1',3a',7a',E)- 7a'-trideuteromethyl-4'-((4,4,5,5-tetramethyl-1,3,2-dioxaboralan-2-yl)methylen)octahydro-1H-inden-1'-yl)hexanoate (rac-43)

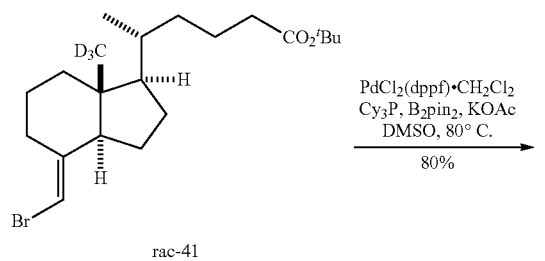

rac-41 rac-43

It is obtained by following the preparation of tert-butyl 5-(R)-[(1',3a',7a',E)- 7a'-methyl-4'-((4,4,5,5-tetramethyl-1,3,2-dioxaboralan-2-yl)methylen)octahydro-1H-inden-1'-yl)hexanoate (rac-42) using rac-41 (0.099 g, 0.248 mmol), Cy₃P (4 mg, 0.015 mmol), Pd(dppf)Cl₂.CH₂Cl₂ (6 mg, 0.007 mmol), KOAc (0.073 g, 0.744 mmol) and Pin₂B₂ (0.126 g, 0.496 mmol) to give rac-43 [0.088 g, 80%, yellow oil]. ¹H-NMR (400 MHz, CDCl₃): δ=4.89 (1H, s, H-4'), 3.15 (1H, m, H-5'), 2.16 (2H, m, H-2), 1.43 (9H, s, ᵗBuO), 1.25 (12H, s, CH₃-pinacol), 0.91 (3H, d, J=6.1, H-6).

EXAMPLE 44

(3R)-Oct-1-en-7-yn-3-ol (1)

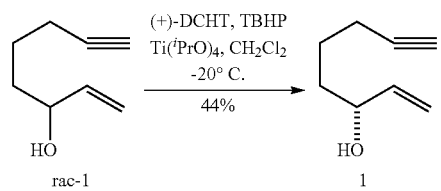

Dicyclohexyltartrate (13.95 g, 44.43 mmol) was added to a solution of rac-1 (4.59 g, 37.02 mmol) in CH₂Cl₂ (120 mL). The mixture was cooled to −20° C. and Ti(ⁱPrO)₄ (10.72 mL, 37.02 mmol) was added. A solution of tert-butylhydroperoxide in decane (4.89 mL, 5 M, 24.43 mmol) was added. The mixture was kept in the fridge at −20° C. After 21 days the reaction was quenched by the addition of FeSO₄.7H₂O and a solution of tartaric acid in H₂O. The aqueous layer was extracted with Et₂O. The organic phase was concentrated and purified by column chromatography (SiO₂, 30% ethyl acetate/hexanes) to afford 1 [2.02 g, 44%, $[\alpha]_D^{25}$ =−6.2 (c=1.8, CHCl₃), colorless oil].

EXAMPLE 45

(3R)-tert-Butyldimethyl(oct-1-en-7-yn-3-yloxy)silane (2)

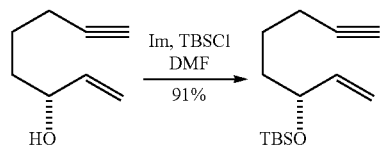

Obtained by following the preparation of (3)-tert-Butyldimethyl(oct-1-en-7-yloxy)silane (rac-2). $[\alpha]_D^{25}$ =−11.8 (c=0.8, CHCl₃).

EXAMPLE 46

(7R)-Benzyl (6-(tert-butyldimethysilyl)oct-7-en-1-yn-1-yl)dimethylsilane (3)

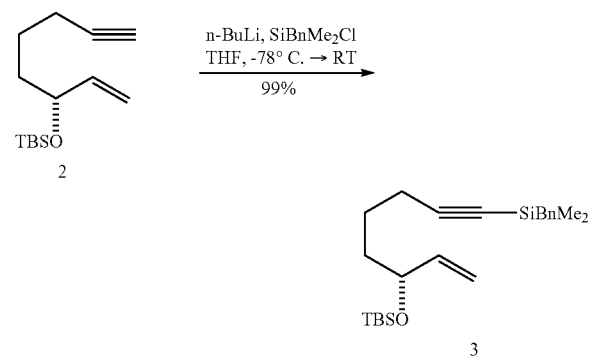

Obtained by following the preparation of (7)-benzyl (6-(tert-butyldimethysilyl)oct-7-en-1-yn-1-yl)dimethylsilane (rac-3). $[\alpha]_D^{25} = -9.1$ (c=1.3, CHCl$_3$).

EXAMPLE 47

(7R,7aR)-3-Benzyldimethylsilyl)-7-(tert-butyldimethylsilyloxy)-5,6,7,7a-tetrahydro-1H-inden-2(4H)-one (4)

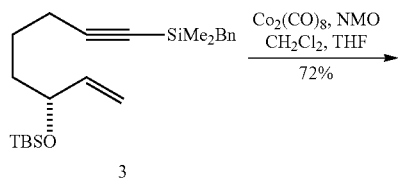

3

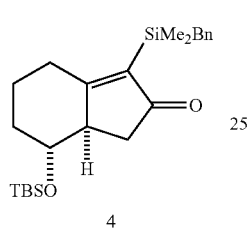

4

Obtained by following the preparation of (7,7a)-3-Benzyldimethylsilyl)-7-(tert-butyl dimethylsilyloxy)-5,6,7,7a-tetrahydro-1H-inden-2(4H)-one (rac-4). $[\alpha]_D^{25} = -26.2$ (c=1.0, CHCl$_3$).

EXAMPLE 48

(2S,7R,7aR)-3-Benzyldimethylsilyl)-7-(tert-butyldimethylsilyloxy)-2,4,5,6,7,7a-hexahydro-1H-inden-2-ol (5)

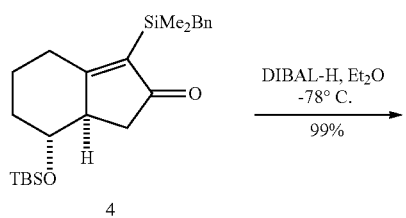

4

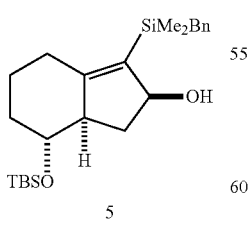

5

Obtained by following the preparation of (2,7,7a)-3-benzyldimethylsilyl)-7-(tert-butyldimethylsilyloxy)-2,4,5,6,7,7a-hexahydro-1H-inden-2-ol (rac-5). $[\alpha]_D^{25} = -23.8$ (c=1.2, CHCl$_3$).

EXAMPLE 49

Benzyl [(3aS,7R,7aR)-7-(tert-butyldimethylsilyl)oxy-3a-methyl-3a,4,5,6,7,7a-hexahydro-1H-inden-3-yl]dimethylsilane (6)

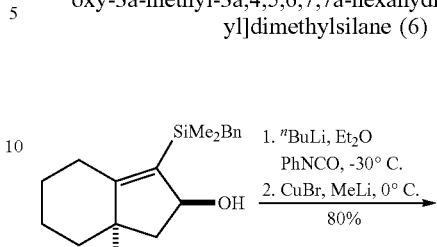

5

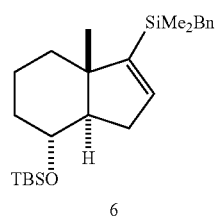

6

Obtained by following the preparation of benzyl [(3a,7,7a)-7-(tert-butyldimethylsilyl)oxy-3a-methyl-3a,4,5,6,7,7a-hexahydro-1H-inden-3-yl]dimethylsilane (rac-6). $[\alpha]_D^{25} = -7.0$ (c=1.6, CHCl$_3$).

EXAMPLE 50

Benzyl [(3aS,7R,7aR)-7-(tert-butyldimethylsilyl)oxy-3a-trideuteromethyl-3a,4,5,6,7,7a-hexahydro-1H-inden-3-yl]dimethylsilane (7)

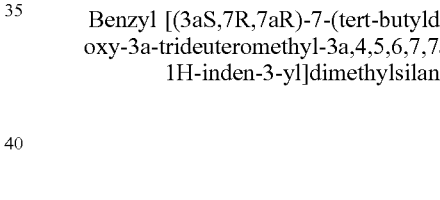

5

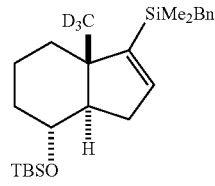

7

Obtained by following the preparation of benzyl [(3,7,7a)-7-(tert-butyldimethylsilyl)oxy-3a-trideuteromethyl-3a,4,5,6,7,7a-hexahydro-1H-inden-3-yl]dimethylsilane (rac-7). $[\alpha]_D^{25} = -7.7$ (c=0.2, CHCl$_3$).

EXAMPLE 51

(3aR,4R,7aS)-4-(tert-Butyldimethylsilyloxy)-7a-trideuteromethyloctahydro-1H-inden-1-one (15)

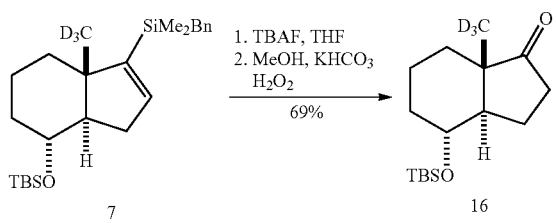

Obtained by following the preparation of (3a,4,7a)-4-(tert-Butyldimethylsilyloxy)-7a-trideuteromethyloctahydro-1H-inden-1-one (rac-15). $[\alpha]_D^{25}$ =65.7 (c=1.5, CHCl$_3$).

EXAMPLE 52

(3aS,7R,7aR)-7-(tert-Butyldimethylsilyloxy)-3a-trideuteromethyl-3a',4',5',6',7',7a'-hexahydro-1H-inden-3-yltrifluoromethanesulfonate (18)

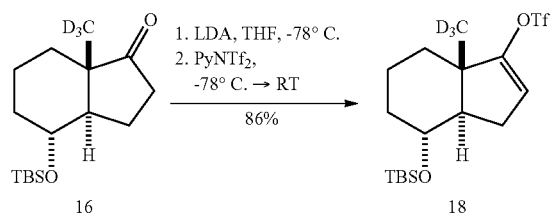 [SMILES: [2H]C([2H])([2H])[C@]12CCC[C@@H](O[Si](C)(C)C(C)(C)C)[C@@H]1CCC2=O ; [2H]C([2H])([2H])[C@]12CCC[C@@H](O[Si](C)(C)C(C)(C)C)[C@@H]1CC=C2OS(=O)(=O)C(F)(F)F]

Obtained by following the preparation of (3a,7,7a)-7-(tert-butyldimethylsilyloxy)-3a-trideuteromethyl-3a',4',5',6',7',7a'-hexahydro-1H-inden-3-yl trifluoromethanesulfonate (rac-17). $[\alpha]_D^{25}$ =13.5 (c=1.6, CHCl$_3$).

EXAMPLE 53

Ethyl (E)-3-((3a'S,7'R,7a'R)-7'-((tert-butyldimethylsilyl)oxy)-3a'-trideuteromethyl-3a',4',5',6',7',7a'-hexahydro-1H-inden-3'-yl)but-2-enoate (21)

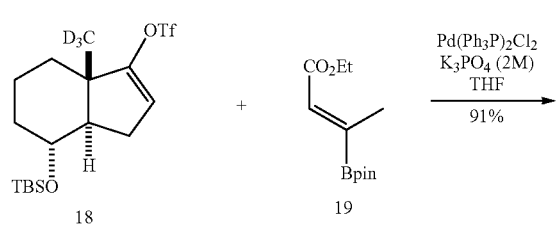

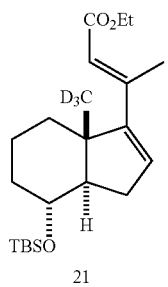

Obtained by following the preparation of ethyl (E)-3-((3a',7',7a')-7'-((tert-butyldimethylsilyl)oxy)-3 a'-trideuteromethyl-3a',4',5',6',7',7a'-hexahydro-1H-inden-3'-yl)but-2-enoate (rac-20). $[\alpha]_D^{25}$ =−35.1 (c=1.2, CHCl$_3$).

EXAMPLE 54

(R)-Ethyl 3-((3a'S,7'R,7a'R)-7'-((tert-butyldimethylsilyl)oxy)-3a'-trideuteromethyl-3a',4',5',6',7',7a'-hexahydro-1H-inden-3'-yl)butanoate (24).

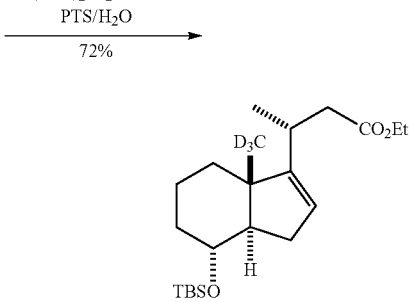

Obtained by following the preparation of (R)-ethyl 3-((3a',7',7a')-7'-((tert-butyldimethylsilyl)oxy)-3a'-trideuteromethyl-3a',4',5',6',7',7a'-hexahydro-1H-inden-3'-yl)butanoate (rac-22). $[\alpha]_D^{25}$ =2.5 (c=1.6, CHCl$_3$).

EXAMPLE 55

(R)-3-((3a'S,7'R,7a'R)-7-(tert-Butyldimethylsilyloxy)-3a'-trideuteromethyl-3a',4',5',6',7',7a'-hexahydro-1H-inden-3'-yl)butan-1-ol (26).

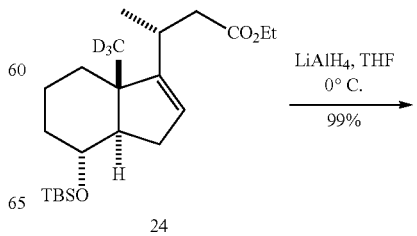

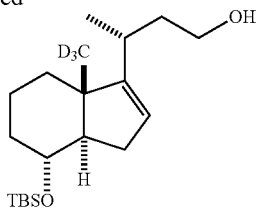

26

Obtained by following the preparation of 3-((3a',7',7a')-7'-(tert-Butyldimethylsilyloxy)-3a'-methyl-3a',4',5',6',7',7a'-hexahydro-1H-inden-3'-yl)butan-1-ol (rac-25). $[\alpha]_D^{25} = -1.3$ (c=1.2, CHCl$_3$).

EXAMPLE 56

(R)-3-((1'R,3a'R,4'R,7a'R)-4'-((tert-Butyldimethylsilyl)oxy)-7a'-trideuteromethyloctahydro-1H-inden-1'-yl)butan-1-ol (28)

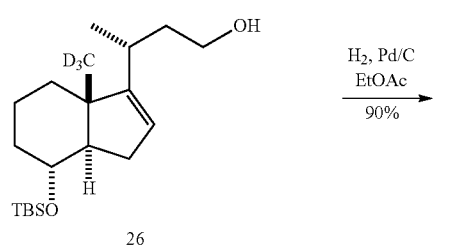

26 → 28

Obtained by following the preparation of 3-((1',3a',4',7a')-4'-((tert-butyldimethylsilyl)oxy)-7a'-methyloctahydro-1H-inden-1'-yl)butan-1-ol (rac-27). $[\alpha]_D^{25} = 5.1$ (c=4.2, CHCl$_3$).

EXAMPLE 57 tert-Butyl [((1'R,3a'R,4'R,7a'R)-1-((R)-4-iodobutan-2-yl)-7a'-trideuteromethyloctahydro-1H-inden-4-yloxy)dimethylsilane (30)

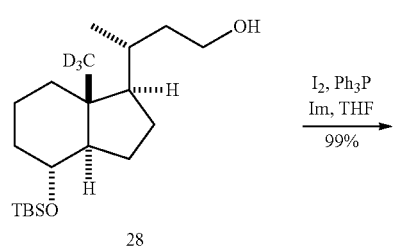

28

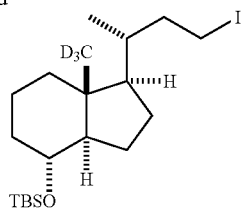

30

Obtained by following the preparation of tert-butyl [((1',3a',4',7a')-1-(4-iodobutan-2-yl)-7a'-methyloctahydro-1H-inden-4'-yloxy)dimethylsilane (rac-29). $[\alpha]_D^{25} = 23.4$ (c=2.9, CHCl$_3$).

EXAMPLE 58 tert-Butyl 5-(R)-[((1'R,3a'R,4'R,7a'R)-4'-(tert-butyldimethylsilyloxy)-7a'-trideuteromethyloctahydro-1H-inden-F-yl)hexanoate (32)

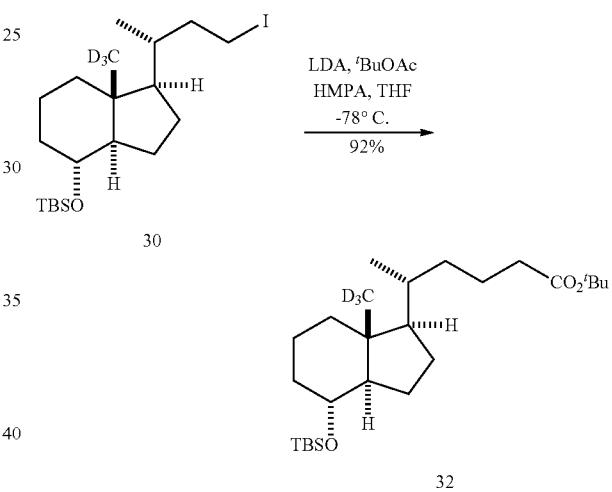

30 → 32

Obtained by following the preparation of tert-butyl 5-(R)-[((1',3a',4',7a')-4'-(tert-butyldimethylsilyloxy)-7a'-methyloctahydro-1H-inden-1'-yl)hexanoate (rac-31). $[\alpha]_D^{25} = 8.7$ (c=3, CHCl$_3$).

EXAMPLE 59

(S)-3-((3a'S,7'R,7a'R)-7'-(tert-Butyldimethylsilyloxy)-3a'-methyl-3a',4',5',6',7',7a'-hexahydro-1H-inden-3'-yl)butan-1-ol (33)

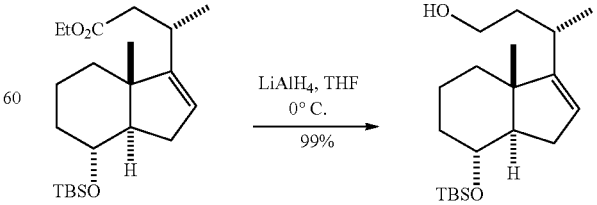

23 → 33

Obtained by following the preparation of (S)-3-((3a',7', 7a')-7'-(tert-Butyldimethylsilyloxy)-3a'-methyl-3a',4',5',6', 7',7a'-hexahydro-1H-inden-3'-yl)butan-1-ol (rac-33). [α]$_D^{25}$ =14.8 (c=1.4, CHCl$_3$).

EXAMPLE 60 tert-Butyl ((3a'S,7R,7a'R)-3'-((S)-4-iodobutan-2-yl)-3a'-methyl-3a',4',5',6',7',7a'-hexahydro-1H-inden-7'-yloxy)dimethylsilane (34)

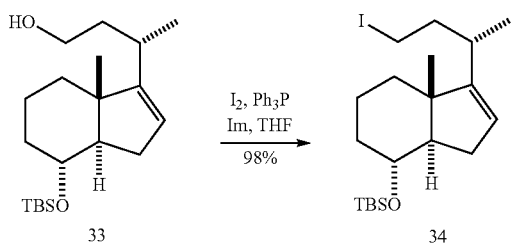

Obtained by following the preparation of tert-butyl ((3a', 7,7a')-3'-((S)-4-iodobutan-2-yl)-3a'-methyl-3a',4',5',6',7',7a'-hexahydro-1H-inden-7'-yloxy)dimethylsilane (rac-34). [α]$_D^{25}$ =15.4 (c=1.4, CHCl$_3$).

EXAMPLE 61 tert-Butyl 5-(S)-[((3a'S,7'R,7a'R)-7'-(tert-butyldimethylsilyloxy)-3a'-methyl-3a',4',5',6',7',7a'-hexahydro-1H-inden-3'-yl)hexanoate (35).

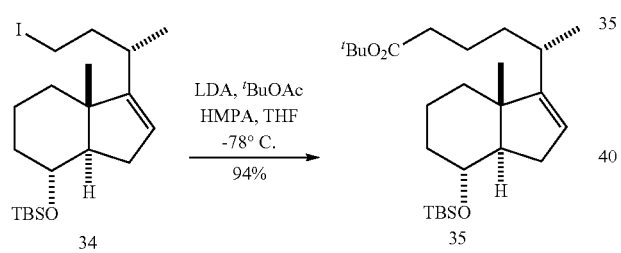

Obtained by following the preparation of tert-butyl 5-[((3a',7',7a')-7'-(tert-butyldimethylsilyloxy)-3a'-methyl-3a',4',5',6',7',7a'-hexahydro-1H-inden-3'-yl)hexanoate (rac-35). [α]$_D^{25}$ =12.4 (c=1.1, CHCl$_3$).

EXAMPLE 62 tert-Butyl 5-(R)-[(1'R,3a'R,4'R,7a'R)-4'-hydroxy-7a'-trideuteromethyloctahydro-1H-inden-1'-yl]hexanoate (37).

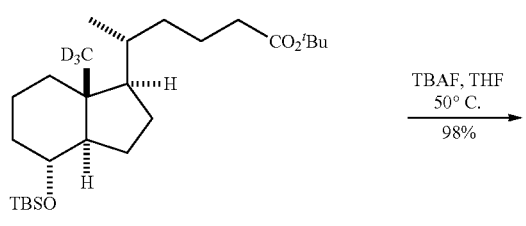

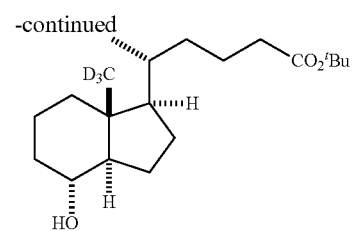

Obtained by following the preparation of tert-butyl 5-((1', 3a',4',7a')-4'-hydroxy-7a'-methyloctahydro-1H-inden-1'-yl) hexanoate (rac-36). [α]$_D^{25}$ =7.6 (c=2.3, CHCl$_3$).

EXAMPLE 63 tert-Butyl 5-(R)-[(1R,3a'R,7a'R)-7a'-trideuteromethyl-4'-oxooctahydro-1H-inden-1'-yl)hexanoate (39).

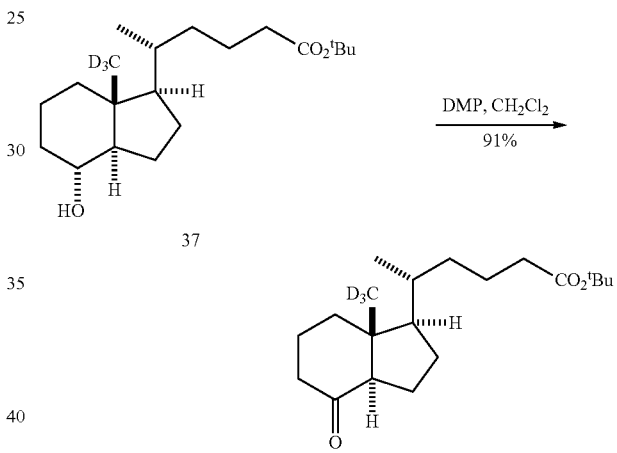

Obtained by following the preparation of tert-butyl 5-(R)-((1',3a',7a')- 7a'-methyl-4'-oxooctahydro-1H-inden-1'-yl) hexanoate (rac-38). [α]$_D^{25}$ =1.7 (c=2.3, CHCl$_3$).

EXAMPLE 64 tert-Butyl 5-(R)-[(1'R,3a'R,7a'R,E)-4-(bromomethylen)-7a'-trideuteromethyl octahydro-1H-inden-1'-yl)hexanoate (41).

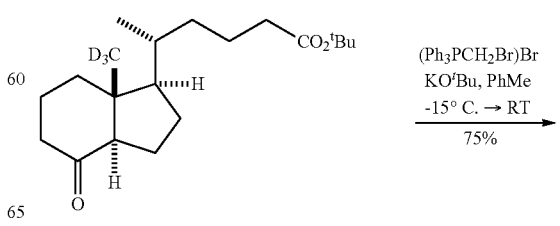

53
-continued

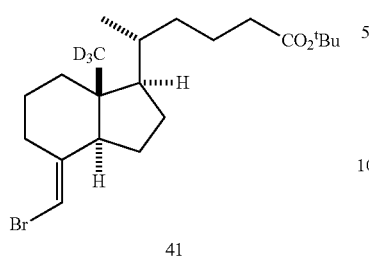

41

Obtained by following the preparation of tert-butyl 5-((1', 3a',7a',E)-4-(bromomethylen)-7a'-methyloctahydro-1H-inden-1'-yl)hexanoate (rac-40). $[\alpha]_D^{25}$ =82.2 (c=2.5, CHCl$_3$).

EXAMPLE 65 tert-Butyl 5-(R)-[(1'R,3a'S,7a'R,E)-7a'-trideuteromethyl-4'-((4,4,5,5-tetramethyl-1,3,2-dioxaboralan-2-yl)methylen)octahydro-1H-inden-1'-yl]hexanoate (43).

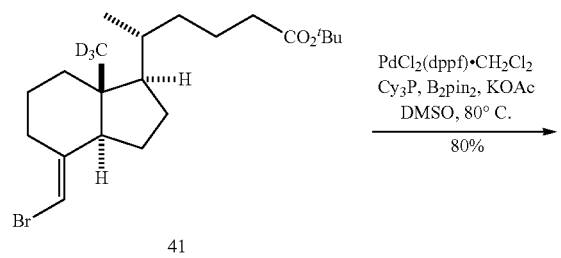

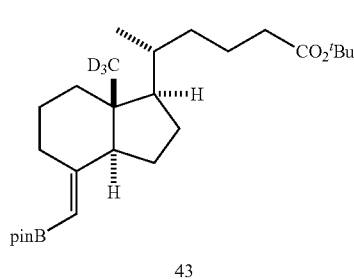

43

Obtained by following the preparation of tert-butyl 5-(R)-[(1',3a',7a',E)- 7a'-methyl-4'-((4,4,5,5-tetramethyl-1,3,2-dioxaboralan-2-yl)methylen)octahydro-1H-inden-1'-yl)hexanoate (rac-42). $[\alpha]_D^{25}$ =62.3 (c=2.3, CHCl$_3$).

54
EXAMPLE 66

18-Trideutero-1α-[(tert-butyldimethyl)oxy]-3-epi-25-(tert-butoxycarbonyl)-26,27-dinorvitamin D$_3$ tritheylsilylether (45)

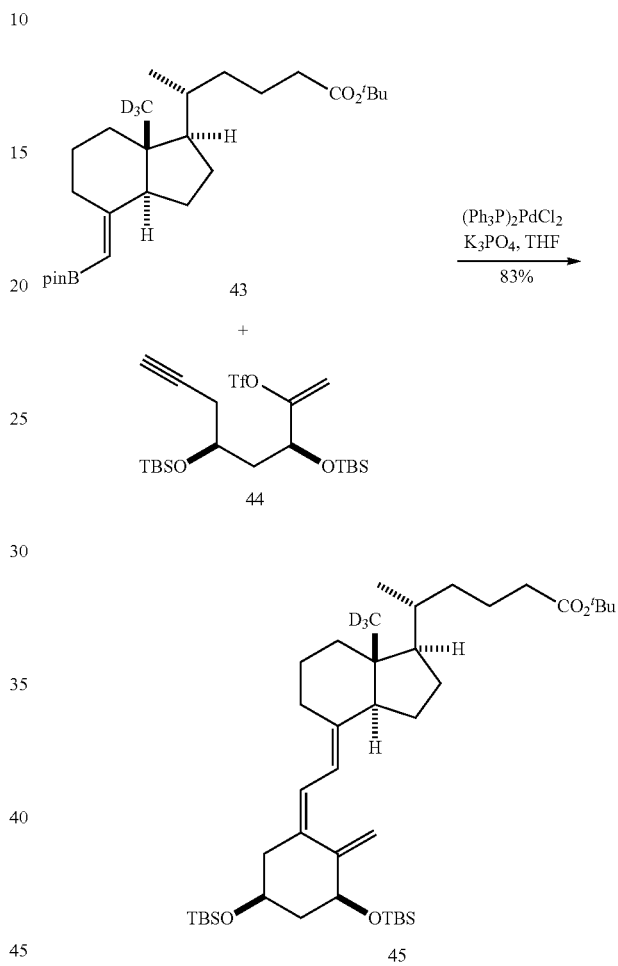

An aqueous solution of K$_3$PO$_4$ (1.34 mL, 2M) was added to a solution of 43 (0.045 g, 0.10 mmol) and 44 (0.063 g, 0.12 mmol) in THF (3 mL). After that (Ph$_3$P)$_2$PdCl$_2$ (4 mg, 0.005 mmol) was added. The reaction mixture protected from light was vigorously stirred. The reaction was quenched with H$_2$O and Et$_2$O. The mixture was extracted with Et$_2$O. The organic phase was concentrated and purified by flash chromatography (SiO$_2$ 50% ethyl acetate/hexanes) to afford 45 [0.057 g, 83%, $[\alpha]_D^{25}$ =−35.6 (c=1.9, CHCl$_3$), colorless oil]. $^1$H-NMR (400 MHz, CDCl$_3$): δ=6.27 (1H, d, J=10.9, H-6), 5.99 (1H, d, J=11.2, H-7), 5.38 (1H, s, H-19), 4.93 (1H, s, H-19), 3.93 (1H, m, H-1), 3.69 (1H, m, H-3), 1.44 (9H, s, $^t$BuO), 0.94 (9H, s,$^t$BuSi), 0.89 (9H, s,$^t$BuSi), 0.10 (3H, s, CH$_3$Si), 0.08 (3H, s, CH$_3$Si), 0.07 (6H, s, 2×CH$_3$Si).

EXAMPLE 67

18-Trideutero-1α-[(triethylsilyl)oxy]-25-(tert-butoxycarbonyl)-26,27-dinorvitamin D$_3$ tritheylsilylether (47)

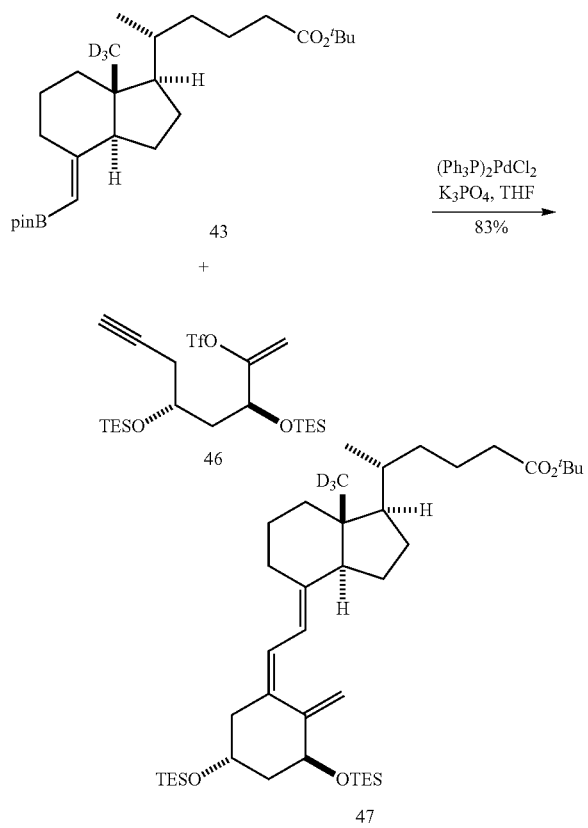

Obtained by following the preparation of 18-trideutero-1a-[(tert-butyldimethylsilyl)oxy]-3-epi-25-(tert-butoxycarbonyl)-26,27-dinorvitamin D$_3$ tritheylsilylether (45) using 43 (0.056 g, 0.14 mmol), 46 (0.086 g, 0.17 mmol), K$_3$PO$_4$ (1.5 mL, 2M) and (Ph$_3$P)$_2$PdCl$_2$(5 mg, 0.007 mmol) to give 47 [0.042 g, 0.102 mmol, 60%, white solid]. $^1$H-NMR (400 MHz, CDCl$_3$): δ=6.24 (1H, d, J=11.3, H-6), 6.04 (1H, d, J=11.2, H-7), 5.21 (1H, s, H-19), 4.88 (1H, s, H-19), 4.39 (1H, m, H-1), 4.20 (1H, m, H-3), 2.20 (2H, m, H-24), 1.44 (9H, s, $^t$BuO), 0.95 (6H, t, J=7.9, CH$_3$-TES), 0.95 (3H, H-21), 0.60 (2H, q, J=7.9, CH$_2$-TES), 0.59 (2H, q, J=7.9, CH$_2$-TES).

EXAMPLE 68

18-Trideutero-26,27-dihomo-1α,25-dihydroxy-3-epi-colecalciferol (48)

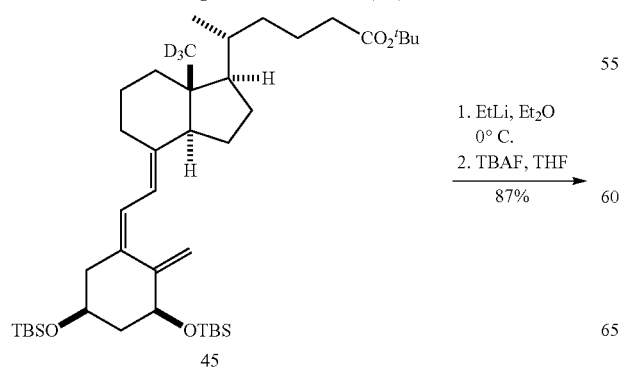

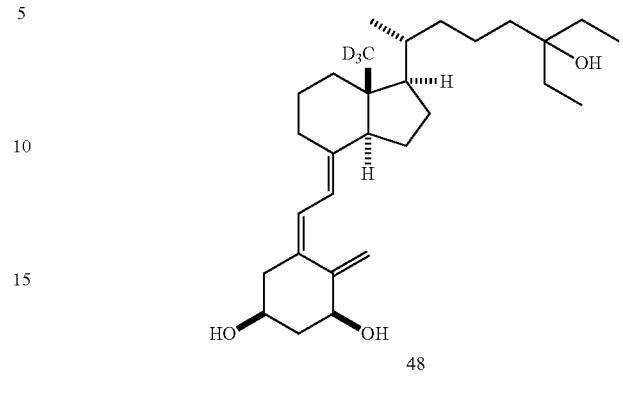

A solution of EtLi in benzene/cyclohexane (0.498 mL, 0.5 M, 0.249 mmol) was added to a solution of 45 (0.057 g, 0.083 mmol) in Et$_2$O (3 mL) at 0° C. After 10 min, the reaction was quenched by addition saturated aqueous solution of NH$_4$Cl. The mixture was extracted with Et$_2$O. The organic phase was concentrated. The residue was dissolved in THF (2 mL) and a solution of TBAF in THF (0.249 mL, 1M, 0.249 mmol) was added. The reaction was quenched by addition of a saturated solution of NH$_4$Cl. The aqueous layer was extracted with ethyl acetate. The organic phase was concentrated and purified by column chromatography (SiO$_2$, 35% ethyl acetate/hexanes) to afford 48 [0.031 g, 87% (two steps), white solid]. $^1$H-NMR (400 MHz, DMSO) δ 6.40 (1H, d, J=11.2, H-6), 5.99 (1H, d, J=11.2, H-7), 5.27 (1H, m, H-19), 4.96 (1H, d, J=2.1, H-19), 4.26 (1H, m, H-1), 4.14 (1H, m, H-3), 2.82 (2H, m), 2.53 (1H, dd, J=13.5, 3.5), 2.39 (2H, m), 1.99 (4H, m), 1.43 (4H, q, J=7.3, CH$_2$CH$_3$), 0.90 (3H, d, J=6.3, H-21), 0.83 (6H, t, J=7.3, CH$_2$CH$_3$).

EXAMPLE 69

18-Trideutero-1α,25-dihydroxy-3-epi-colecalciferol (49)

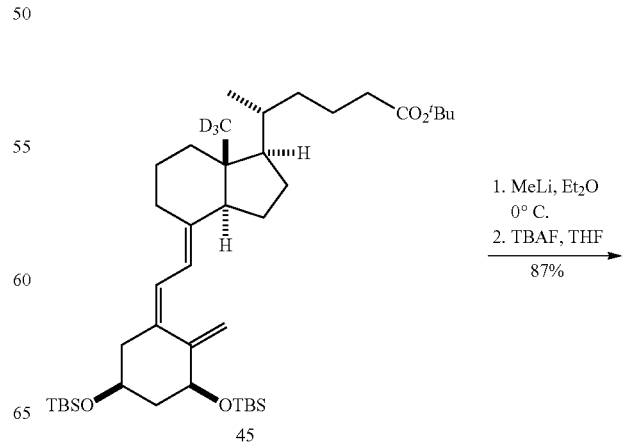

-continued

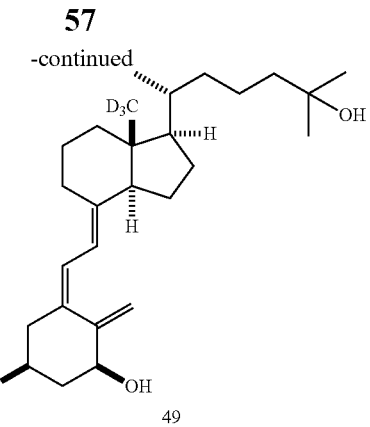

49

Obtained by following the preparation of 18-trideutero-26,27-dihomo-1α,25-dihydroxy-3-epi-colecalciferol (48) using 45 (0.065 g, 0.095 mmol), MeLi (0.120 mL, 1.6 M, 0.190 mmol), TBAF (0.288 mL, 1 M, 0.288 mmol) to give 49 [0.023 g, 87% (two steps), white solid]. $^1$H-NMR (500 MHz, CDCl$_3$) δ 6.43 (1H, dd, J=11.2, H-6), 6.02 (1H, dd, J=11.3, H-7), 5.29 (1H, s, H-19), 5.00 (1H, d, J=1.7, H-19), 4.31 (1H, d, J=4.5, H-1), 4.05 (1H, m, H-3), 2.84 (1H, dm, J=12.5, H-9), 2.56 (1H, dd, J=13.5, 2.3, H-4α), 2.43 (1H, dd, J$_1$=13.4, 5.7, H-4β), 2.07 (1H, dt, J$_1$=13.5, 3.6, H-12), 1.21 (6H, s, H-26 and H-27), 0.94 (3H, d, J=6.5, CH$_3$-21).

EXAMPLE 70

18-Trideutero-1α,25-dihydroxy-colecalciferol (50)

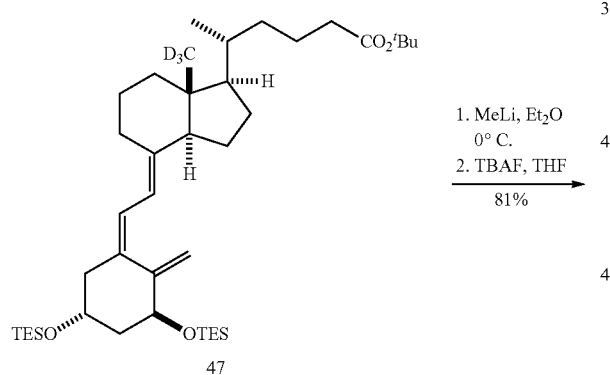

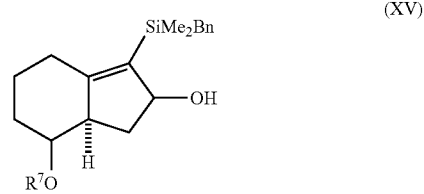

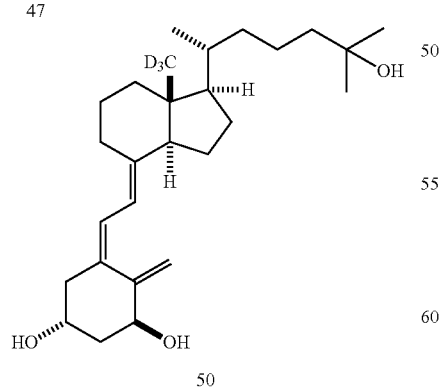

50

Obtained by following the preparation of 18-trideutero-1α,25-dihydroxy-3-epi-colecalciferol (49) using 47 (0.036 g, 0.052 mmol), MeLi (0.098 mL, 1.6 M, 0.156 mmol), TBAF (0.130 mL, 1 M, 0.130 mmol) to give 50 [0.018 g, 81% (two steps), white solid]. $^1$H-NMR (500 MHz, CD$_3$OD): δ=6.32 (1H, d, J=11.0, H-6), 6.09 (1H, d, J=11.1, H-7), 5.29 (1H, s, H-19), 4.90 (1H, s, H-19), 4.35 (1H, m, H-1), 4.14 (1H, m, H-3), 1.17 (6H, s, H-26), 0.97 (3H, d, J=6.4, H-21).

The invention claimed is:

1. A process for preparing compounds of formula (XIV), comprising:
   a) reacting a compound of formula (XV) with a base and an isocyanate comprising phenyl, t-butyl, p-methylphenyl, or o-methylphenyl isocyanate to form a mixture comprising a carbamate,

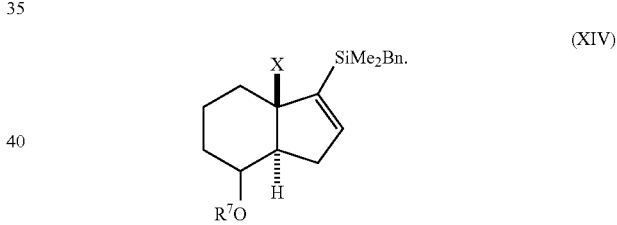

wherein R$^7$ is —SiP$^1$P$^2$P$^3$, each of P$^1$, P$^2$, P$^3$ is independently selected from the group consisting of alkyl, aryl, arylalkyl and heterocycle,
   b) adding a copper salt and X—Li to the mixture of step a), wherein X is selected from the group consisting of hydrogen, (C$_1$-C$_6$) alkyl, aryl, arylalkyl, heteroalkyl and heterocycle, and
   c) obtaining compounds of formula (XIV):

2. A process for preparing compounds of formula (XIV), comprising:
   1) preparing compounds of formula (XVI)

by:
protecting the hydroxyl group of oct-1-en-7-yn-3-ol;
treating the resulting compound with a base and adding a silylating agent; and
performing a Pauson-Khand reaction with the resultant compound of said treating using a CO donor metal complex and a cooxidant;
2) reacting a compound of formula (XVI) with a reducing agent to prepare compounds of formula (XV)

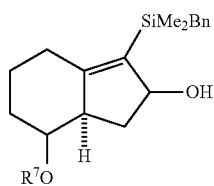

(XV)

wherein R⁷ is —SiP¹P²P³, each of P¹, P², P³ is independently selected from the group consisting of alkyl, aryl, arylalkyl and heterocycle 3) reacting a compound of formula (XV) with a base and an isocyanate comprising phenyl, t-butyl, p-methylphenyl, or o-methylphenyl isocyanate to form a mixture comprising a carbamate, and adding a copper salt and X—Li to the mixture to prepare compounds of formula (XIV), wherein X is selected from the group consisting of hydrogen, ($C_1$-$C_6$) alkyl, aryl, arylalkyl, heteroalkyl and heterocycle; and c) obtaining compounds of formula (XIV):

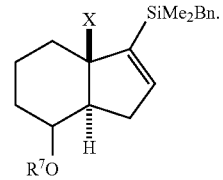

(XIV)

3. A process according to claim 1, wherein the base is lithium diisopropylamide, methyllithium, ethyllithium, n-propyl lithium, i-propyl lithium, n-butyl lithium, hexyl lithium, phenyllithium, pyridine, triethylamine, or ethyldiisopropylamine.

* * * * *